(12) United States Patent
Jippo et al.

(10) Patent No.: US 11,702,438 B2
(45) Date of Patent: Jul. 18, 2023

(54) COMPOUND, NANORIBBON, AND SEMICONDUCTOR DEVICE

(71) Applicants: FUJITSU LIMITED, Kawasaki (JP); National University Corporation Nara Institute of Science and Technology, Ikoma (JP)

(72) Inventors: Hideyuki Jippo, Atsugi (JP); Manabu Ohtomo, Kawasaki (JP); Hironobu Hayashi, Ikoma (JP); Hiroko Yamada, Ikoma (JP)

(73) Assignees: FUJITSU LIMITED, Kawasaki (JP); NATIONAL UNIVERSITY CORPORATION NARA INSTITUTE OF SCIENCE AND TECHNOLOGY, Ikoma (JP)

( * ) Notice: Subject to any disclaimer, the term of this patent is extended or adjusted under 35 U.S.C. 154(b) by 0 days.

(21) Appl. No.: 17/851,657

(22) Filed: Jun. 28, 2022

(65) Prior Publication Data
US 2022/0332743 A1    Oct. 20, 2022

Related U.S. Application Data

(62) Division of application No. 16/777,450, filed on Jan. 30, 2020, now Pat. No. 11,401,291.

(30) Foreign Application Priority Data

Feb. 28, 2019   (JP) ................. 2019-036472

(51) Int. Cl.
| | | |
|---|---|---|
| C07F 15/00 | (2006.01) | |
| C07D 403/00 | (2006.01) | |
| H01B 1/12 | (2006.01) | |
| C07F 15/06 | (2006.01) | |
| C07D 403/14 | (2006.01) | |

(Continued)

(52) U.S. Cl.
CPC .......... C07F 15/065 (2013.01); C07D 403/14 (2013.01); C07F 3/02 (2013.01);
(Continued)

(58) Field of Classification Search
CPC ...... C07F 1/08; C07F 3/02; C07F 3/06; C07F 7/28; C07F 15/02; C07F 15/04;
(Continued)

(56) References Cited

U.S. PATENT DOCUMENTS

| | | | |
|---|---|---|---|
| 11,401,291 B2 * | 8/2022 | Jippo | .................. C07D 403/14 |
| 2015/0280012 A1 | 10/2015 | Sato et al. | |
| 2016/0290956 A1 | 10/2016 | Sato et al. | |

FOREIGN PATENT DOCUMENTS

| | | |
|---|---|---|
| JP | 2007-027190 A | 2/2007 |
| JP | 2007-194360 A | 8/2007 |

(Continued)

OTHER PUBLICATIONS

Cai et al., "Atomically precise bottom-up fabrication of graphene nanoribbons", Nature, vol. 466, Jul. 22, 2010, pp. 170-473, cited in specification. (4 pages).

(Continued)

*Primary Examiner* — Mark Kopec
(74) *Attorney, Agent, or Firm* — WHDA, LLP

(57) ABSTRACT

A nanoribbon includes a structure represented by a structural formula (8), where g, p, q, r, s, t, and u are mutually independent and are integers greater than or equal to 1, $R^1$, $R^2$, $R^3$, $R^4$, $R^5$, $R^6$, $R^7$, and $R^8$ are mutually independent and are one of a hydrogen atom, a substituent, an alkyl moiety, a phenyl moiety, and a halogen atom, and A denotes a hydrogen atom or an aryl group.

(Continued)

(8)

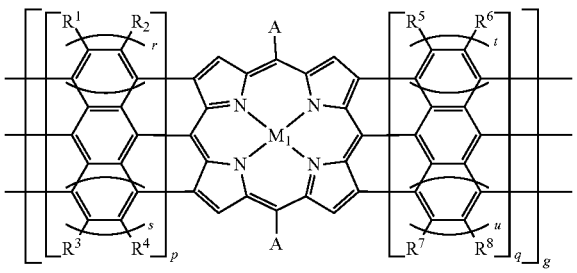

7 Claims, 31 Drawing Sheets

(51) Int. Cl.

| | | |
|---|---|---|
| *C07F 3/02* | (2006.01) | |
| *C07F 7/28* | (2006.01) | |
| *C07F 15/02* | (2006.01) | |
| *C07F 15/04* | (2006.01) | |
| *B82Y 30/00* | (2011.01) | |
| *B82Y 40/00* | (2011.01) | |

(52) U.S. Cl.
CPC .............. *C07F 7/28* (2013.01); *C07F 15/025* (2013.01); *C07F 15/045* (2013.01); *H01B 1/12* (2013.01); *B82Y 30/00* (2013.01); *B82Y 40/00* (2013.01)

(58) Field of Classification Search
CPC ........ C07F 15/06; C07F 17/00; C07D 403/00; C07D 403/14; C07D 487/00; H01B 1/12
See application file for complete search history.

(56) References Cited

FOREIGN PATENT DOCUMENTS

| | | |
|---|---|---|
| JP | 2015-191975 A | 11/2015 |
| JP | 2016-090510 A | 5/2016 |
| JP | 2016-194424 A | 11/2016 |
| WO | 2013/175342 A1 | 11/2013 |

OTHER PUBLICATIONS

Tsuda et al., "Fully Conjugated Porphyrin Tapes with Electronic Absorption Bands That Reach into Infrared", Science, vol. 293, Jul. 6, 2001, pp. 79-82, cited in specification. (5 pages).
Nguyen et al., "Adsorption of diatomic molecules on iron tape-porphyrin: A comparative study", Physical Review, B 77, 195307, 2008, pp. 1-7, cited in specification. (7 pages).
Extended Search Report dated Jul. 15, 2020, issued in counterpart EP Application No. 20154374.1 (11 pages).
Sooambar, Chloe et al., "Synthesis, photophysical, electrochemical, and electrochemiluminescent properties of 5, 15-bis(9-anthracenyl)porphyrin derivatives", Organic & Biomolecular Chemistry, vol. 7, No. 11, Jan. 1, 2009, p. 2402-2413; Cited in EESR dated Jul. 15, 2020.
Davis, Mia et al., "Anthracenylporphyrins", Zeitschrift fur Naturforschung B, vol. 65, Issue 12 (2010), Jun. 2, 2014, 4 pages; Cited in EESR dated Jul. 15, 2020.
Haq, Sam et al., "Clean Coupling of Unfunctionalized Porphyrins at Surfaces To Give Highly Oriented Organometallic Oligomers", Journal of the American Chemical Society, 2011, p. 12031-12039(9 pages).
Su, Xuelei et al., "Edge State Engineering of Graphene Nanoribbons", Nano Letters 2018 18, DOI: 10.1021/acs.nanolett.8b02356, p. 5744-5751 (8 pages).
Li, Jingcheng et al., "Survival of spin state in magnetic porphyrins contacted by graphene nanoribbons", Science Advances, Feb. 16, 2018, DOI: 10.1126/sciadv.aaq0582, p. 1-6 (7 pages).
Zhang et al. "Study on the electronic structures and transport properties of the polyporhyrin nanoribbons with different edge configurations", Physics Letters A 382 (2018) 2769-2775.
Pijeat et al. "Synthesis and Suzuki-Miyaura cross coupling reactions for post-synthetic modification of a tetrabromo-anthracenyl porphyrin", Org. Biomol. Chem., 2018, 16, 8106.
Suzuki et al. "Improved synthesis of meso-Aryl-Substituted [26] Hexaphyrins", Organic Letters 2003, vol. 5, No. 21, 3943-3946.
Davis et al. "Expanding the porphyrin pi-system by fusion with anthracene", Organic Letters 2008, vol. 10, No. 18, 3945-3947.
Office Action dated Oct. 4, 2022, issued in counterpart JP application No. 2019-036472, with English translation. (5 pages).

* cited by examiner

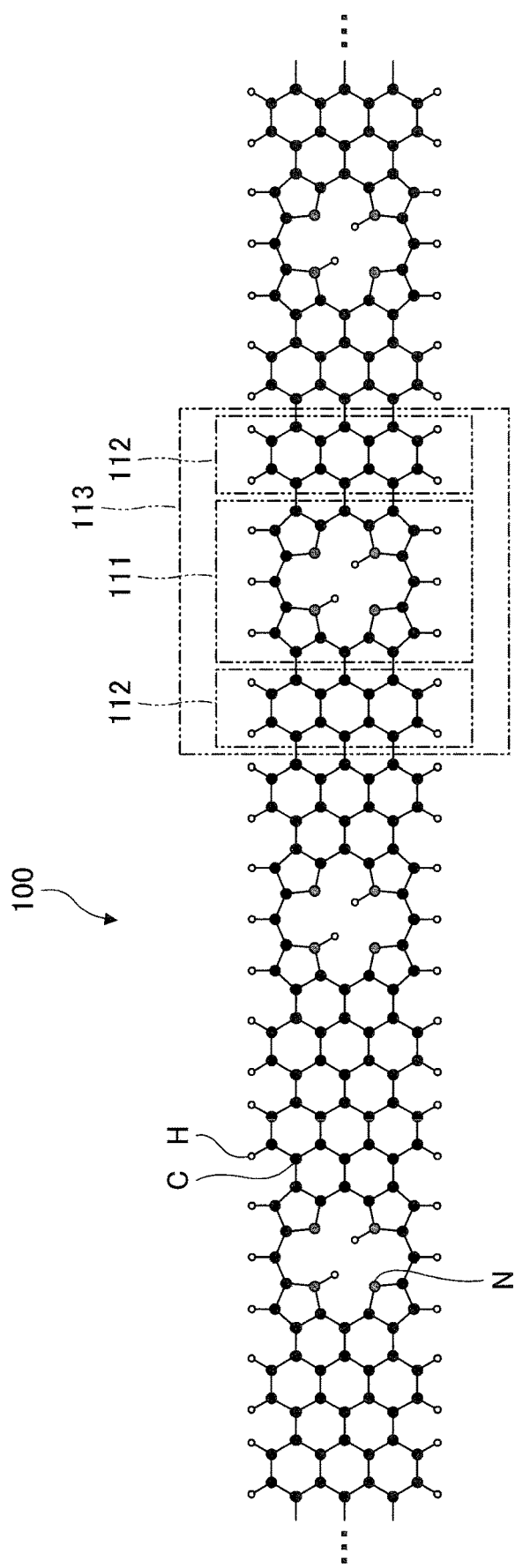

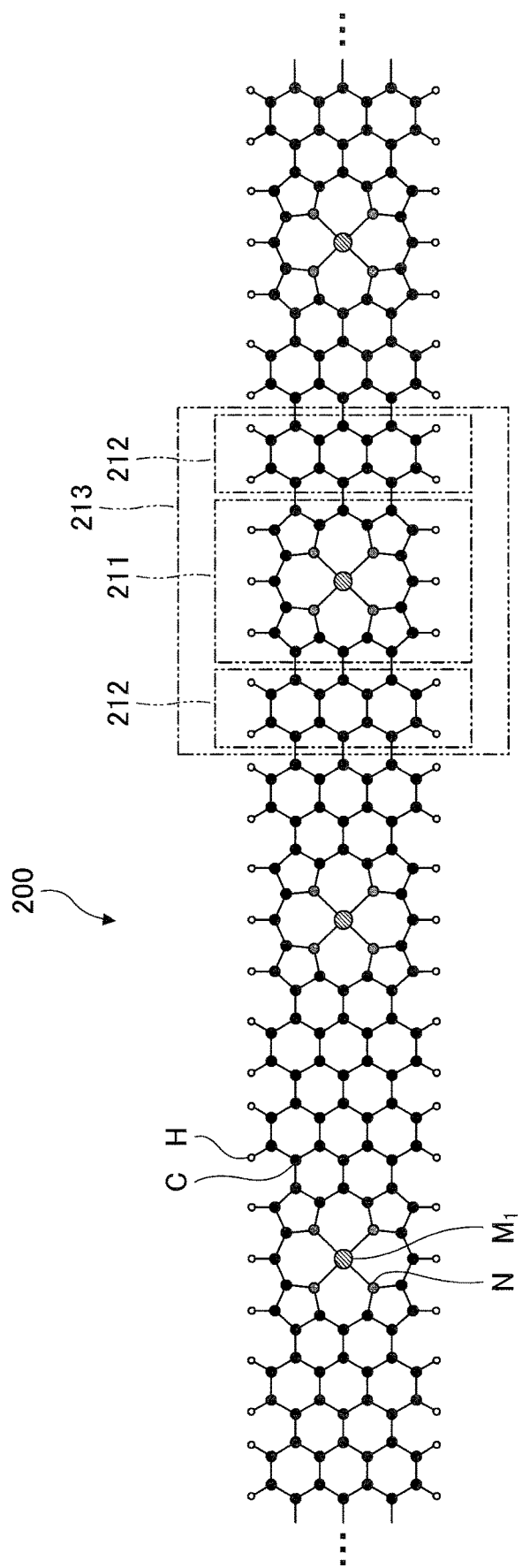

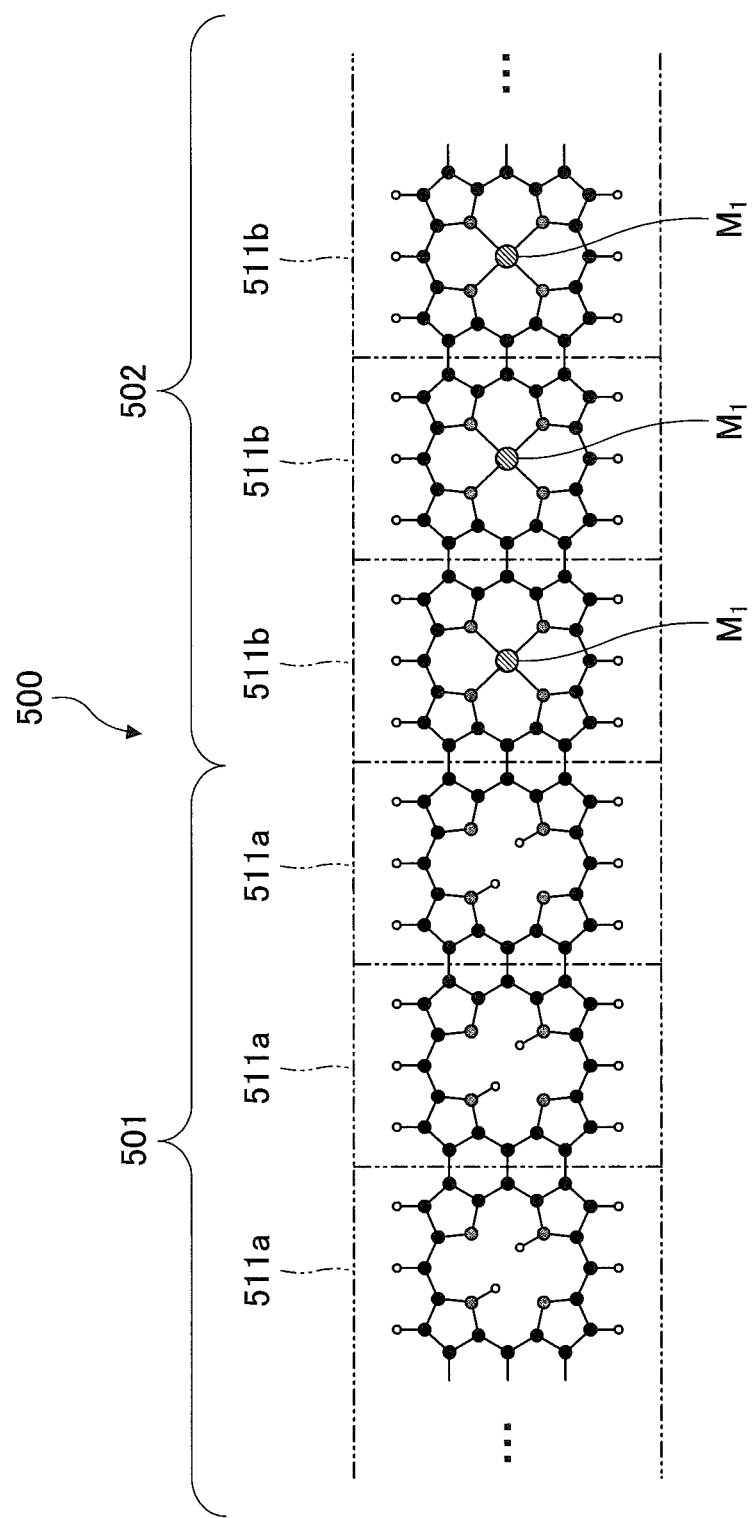

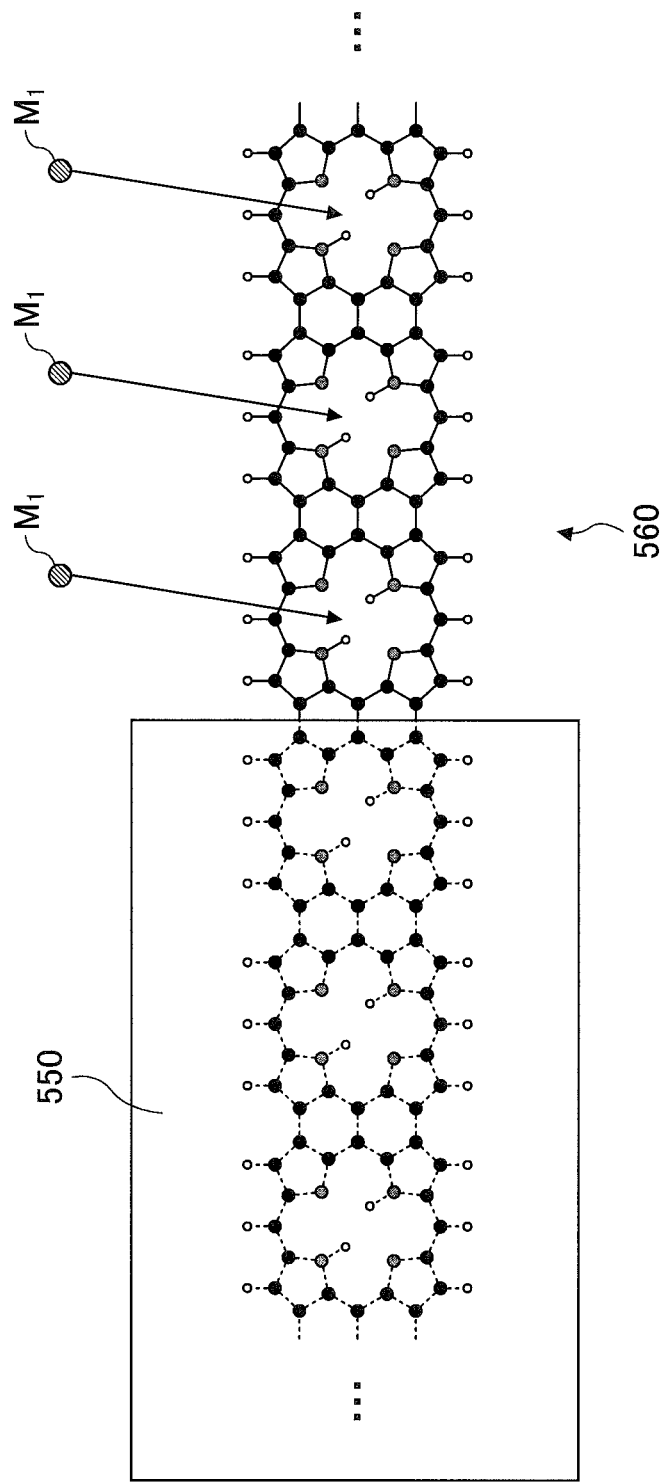

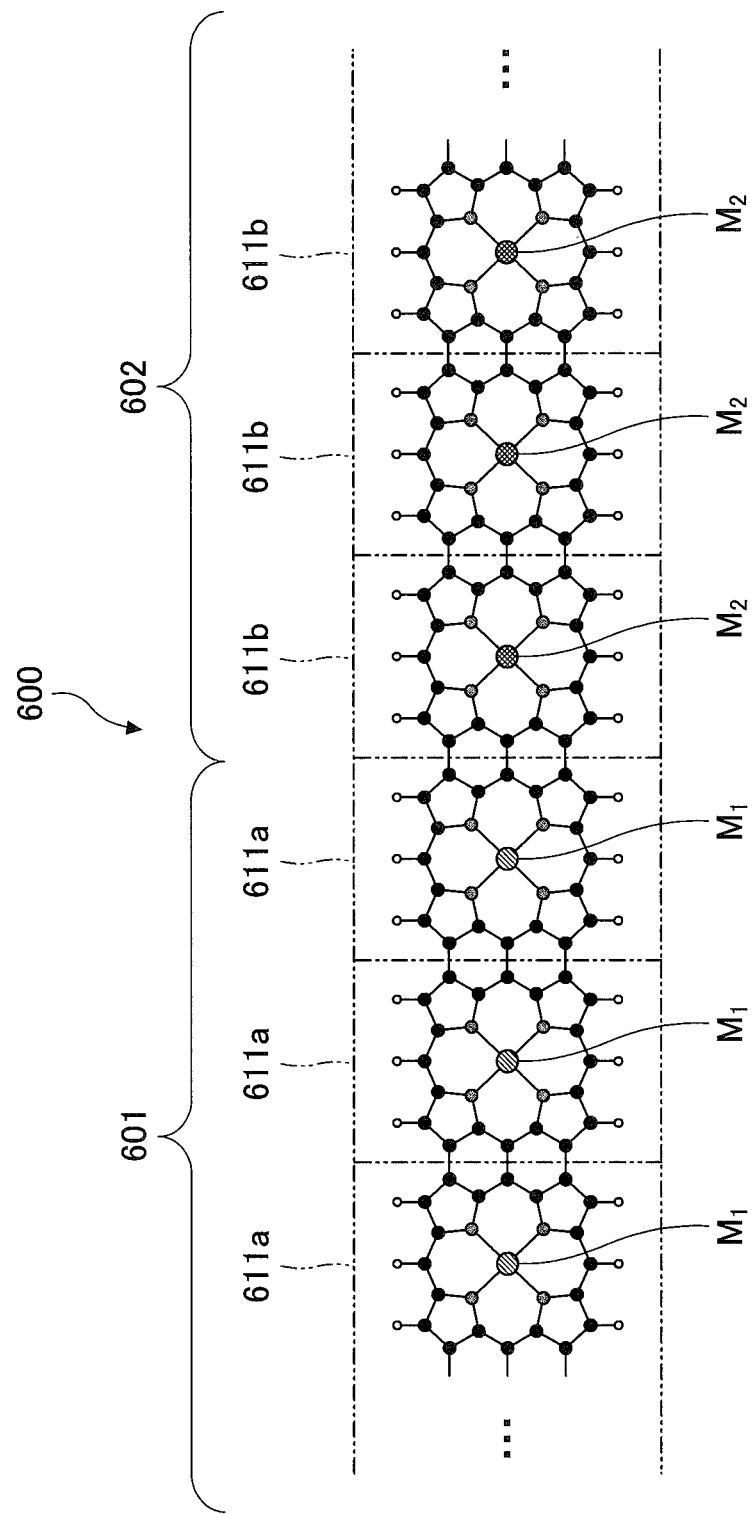

COMPOUND, NANORIBBON, AND SEMICONDUCTOR DEVICE

CROSS-REFERENCE TO RELATED APPLICATIONS

This is a Division of U.S. patent application Ser. No. 16/777,450 filed Jan. 30, 2020, now U.S. Pat. No. 11,401,291, which claims priority under 35 U.S.C. Section 119 to Japanese Patent Application No. 2019-036472 filed on Feb. 28, 2019, the entire contents of which is herein incorporated by reference.

FIELD

The embodiments discussed herein are related to a compound, a nanoribbon, and a semiconductor device.

BACKGROUND

Graphene, which is a two-dimensional material having an extremely high charge mobility, is regarded as a material that may overcome refining limits of Large Scale Integrated (LSI) circuits. Because the graphene has a high mobility of approximately 100,000 $cm^2/Vs$ at room temperature and the electron mobility and the hole mobility do not differ, the graphene is expected for use as a channel material of future electronic devices. However, since the graphene has no band gap, the graphene as it is has a small on-off ratio, thereby making it difficult for use in switching elements.

On the other hand, in nano-sized graphene, a difference between the number of C atoms at the edge and the number of C atoms on the inner side of the edge is small, and the effects of the shape of the graphene itself and the shape at the edge are large, thereby making the graphene exhibit characteristics that differ greatly from the characteristics of bulk graphene. Known nano-sized graphenes include a ribbon-shaped quasi-one-dimensional graphene having a width of several nm, such as the so-called Graphene Nano-Ribbon (GNR). For example, the GNR may be synthesized by polymerizing a precursor compound. This method of synthesizing the GNR may be referred to as the bottom-up synthesis or the bottom-up technique. The characteristics of the GNR greatly change depending on the edge structure and the ribbon width.

The edge structure of the GNR includes two kinds, namely, the arm-chair edge in which the C atoms are arranged at a period of 2 atoms, and the zigzag edge in which the C atoms are arranged in a zigzag. In the arm-chain edge type GNR (AGNR), a finite number of band gaps spread due to the quantum-confined effect and the edge effect, causing the AGNR to exhibit semiconductor-like properties. On the other hand, the zigzag type GNR (ZGNR) exhibits metal-like properties.

The characteristics of the GNR greatly change also depending on the edge modifier. Hence, a heterojunction semiconductor device has been proposed in which the edge modifier bonds different GNRs.

However, electron states of the GNRs manufactured using conventional precursor molecules are limited, and it is difficult to produce various electron states. For example, it is difficult to vary the conductivity type and the band gap of the conventional GNRs.

Further, nanoribbons including continual porphyrin rings, called porphyrin tapes or tape porphyrin, are also known. However, it is also difficult to vary the conductivity type and the band gap of the nanoribbons.

Applicants are aware of the following documents.
Japanese Laid-Open Patent Publication No. 2007-027190
Japanese Laid-Open Patent Publication No. 2007-194360
Japanese Laid-Open Patent Publication No. 2016-090510
Japanese Laid-Open Patent Publication No. 2015-191975
Japanese Laid-Open Patent Publication No. 2016-194424
Jinming Cai et al., "Atomically precise bottom-up fabrication of graphene nanoribbons", Nature, Vol. 466, 22 July 2010, pp. 470-473
Akihiko Tsuda et al., "Fully Conjugated Porphyrin Tapes with Electronic Absorption Bands That Reach into Infrared", Science, Vol. 293, 6 Jul. 2001, pp. 79-82
Tien Quang Nguyen et al., "Adsorption of diatomic molecules on iron tape-porphyrin: A comparative study", Physical Review, B 77, 195307, 2008, pp. 1-7

SUMMARY

Accordingly, it is an object in one aspect of the embodiments to provide a compound, a nanoribbon, and a semiconductor device, which can obtain various electron states.

According to one aspect of the embodiments, a compound is represented by a structural formula (1) or a structural formula (2), where p, q, r, s, t, and u are mutually independent and are integers greater than or equal to 1, $R^1$, $R^2$, $R^3$, $R^4$, $R^5$, $R^6$, $R^7$, and $R^8$ are mutually independent and are one of a hydrogen atom, a substituent, an alkyl moiety, a phenyl moiety, and a halogen atom, and A denotes a hydrogen atom or an aryl group.

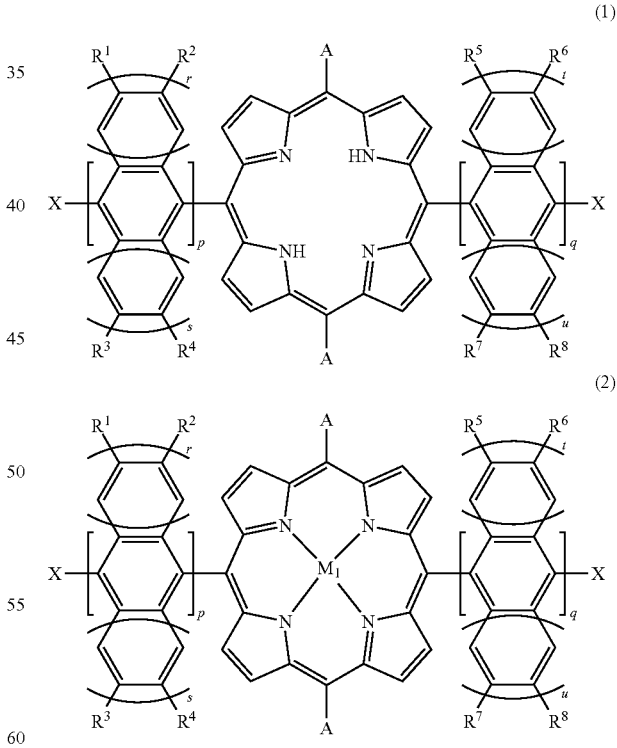

According to another aspect of the embodiments, a method of manufacturing a compound includes coupling a first compound represented by a structural formula (3), a second compound represented by a structural formula (4), and a third compound represented by a structural formula (5), to synthesize a fourth compound represented by a structural formula (6), where p, q, r, s, t, and u are mutually independent and are integers greater than or equal to 1, $R^1$, $R^2$, $R^3$, $R^4$, $R^5$, $R^6$, $R^7$, and $R^8$ are mutually independent and are one of a hydrogen atom, a substituent, an alkyl moiety, a phenyl moiety, and a halogen atom, and A denotes a hydrogen atom or an aryl group.

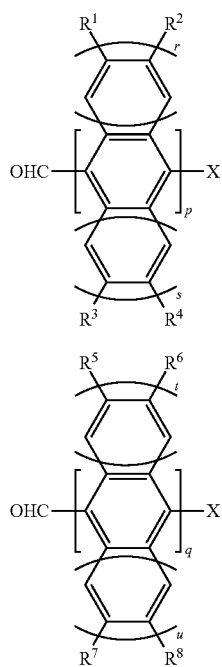

(3)

(4)

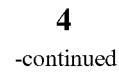

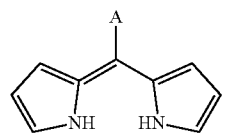

(5)

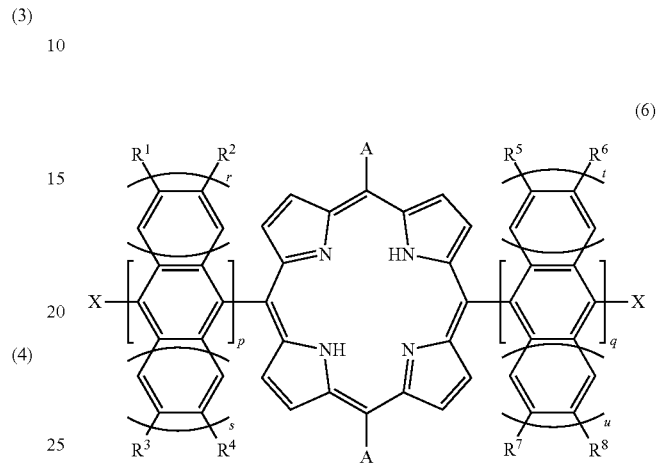

(6)

According to a further aspect of the embodiments, a nanoribbon includes a structure represented by a structural formula (8) or (9), where g or h, p, q, r, s, t, and u are mutually independent and are integers greater than or equal to 1, $R^1$, $R^2$, $R^3$, $R^4$, $R^5$, $R^6$, $R^7$, and $R^8$ are mutually independent and are one of a hydrogen atom, a substituent, an alkyl moiety, a phenyl moiety, and a halogen atom, and A denotes a hydrogen atom or an aryl group.

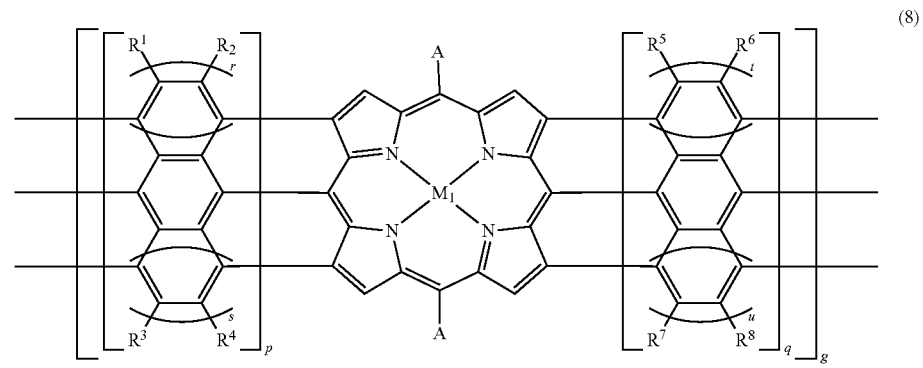

(8)

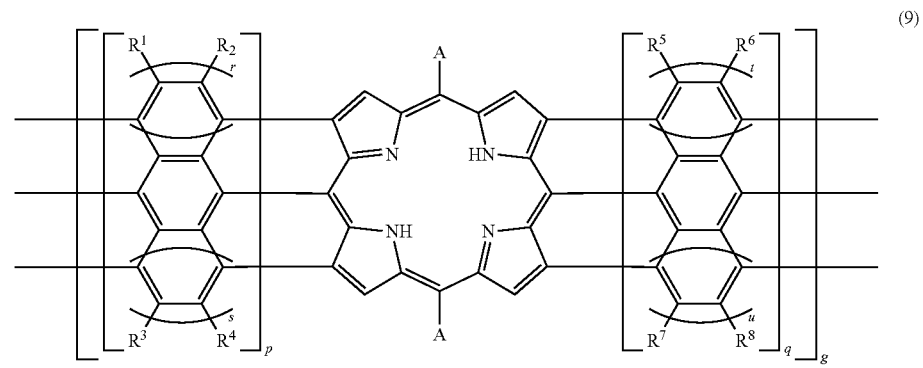

(9)

According to another aspect of the embodiments, a nanoribbon includes a first unit having a structure including an arrangement of a plurality of first sub-units respectively including a structure represented by a structural formula (10); and a second unit having a structure including an arrangement of a plurality of second sub-units respectively including a structure represented by a structural formula (11) or (12), wherein the first unit and the second unit are mutually bonded by a carbon-to-carbon bonding between an end of the first unit and an end of the second unit, and wherein $M_1$ denotes a metal atom or $M_1$ and $M_2$ denote mutually different metal atoms, and A denotes a hydrogen atom or an aryl group.

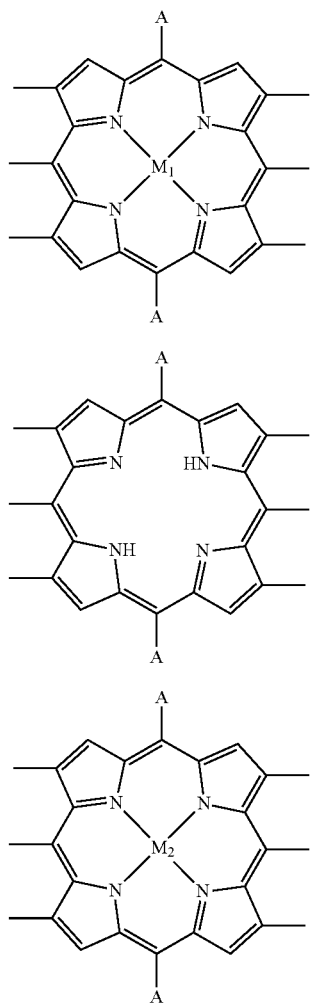

According to still another aspect of the embodiments, a method of manufacturing a nanoribbon, includes generating a dehalogenation reaction in the compound referred above, to obtain a polymer; and generating a dehydrocyclization reaction in the polymer.

According to a further aspect of the embodiments, a semiconductor device includes a substrate; the nanoribbon referred above and provided on the substrate; source and drain electrodes provided on the nanoribbon at respective ends of the nanoribbon; an insulating layer provided on the nanoribbon; and a gate electrode formed on the insulating layer at a position between the source and drain electrodes.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 1 is a diagram illustrating GNR according to a first embodiment;

FIG. 6 is a diagram illustrating the GNR according to a second embodiment;

FIG. 14 is a diagram illustrating a nanoribbon according to a fifth embodiment;

FIG. 15B is a diagram illustrating the method of manufacturing the nanoribbon according to the fifth embodiment;

FIG. 16 is a diagram illustrating the nanoribbon according to a sixth embodiment;

DESCRIPTION OF EMBODIMENTS

Preferred embodiments of the present invention will be described with reference to the accompanying drawings.

A description will now be given of a compound, a nanoribbon and a semiconductor device according to each embodiment of the present invention.

First Embodiment

A first embodiment will be described. The first embodiment relates to Graphene Nano-Ribbon (GNR). FIG. 1 is a diagram illustrating the GNR according to the first embodiment.

GNR 100 according to the first embodiment has a structure in which sub-units 113, each including 2 rows of anthracene 112 bonded to a porphine ring 111, are arranged as illustrated in FIG. 1. In other words, the GNR 100 has a structure in which each of p, q, r, s, t, and u is 1, each of $R^1$, $R^2$, $R^3$, $R^4$, $R^5$, $R^6$, $R^7$, and $R^8$ is hydrogen (H), and A is H in the above-mentioned structural formula (9). The GNR 100 includes a chemical structure of porphyrin.

Figure 2A:
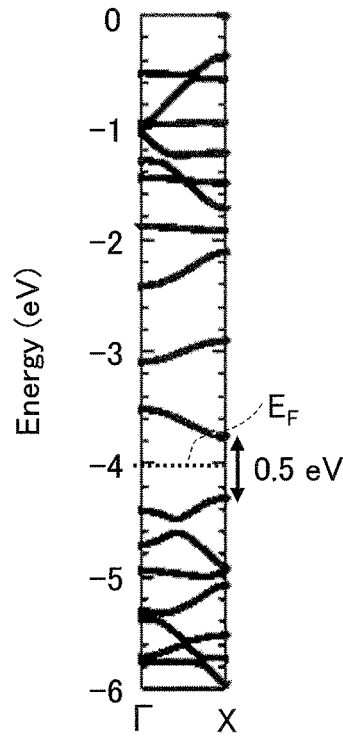
FIG. 2A is a diagram illustrating a band structure of the GNR according to the first embodiment.
Figure 2B:
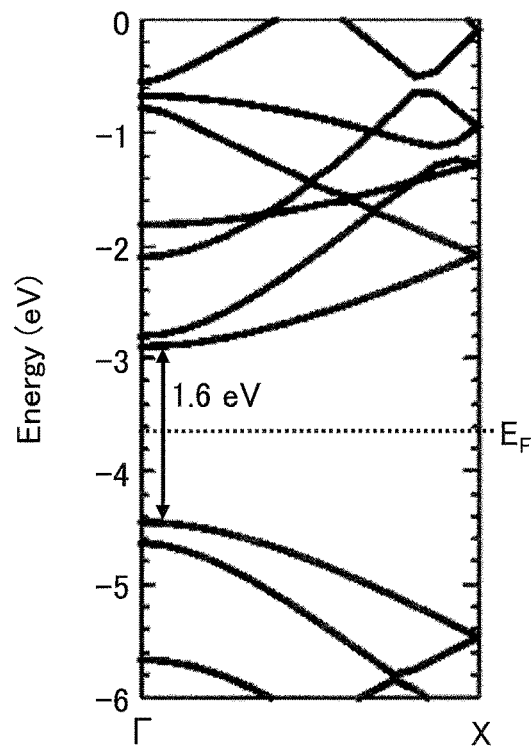
FIG. 2B is a diagram illustrating a band structure of hydrogen-terminated GNR.

Next, a band structure of the GNR 100 will be described. FIG. 2A and FIG. 2B are diagrams illustrating band structures of GNRs predicted according to computations employing a first principle. FIG. 2A illustrates the band structure of the GNR 100, and FIG. 2B illustrates the band structure of a hydrogen-terminated GNR 150.

Figure 3:
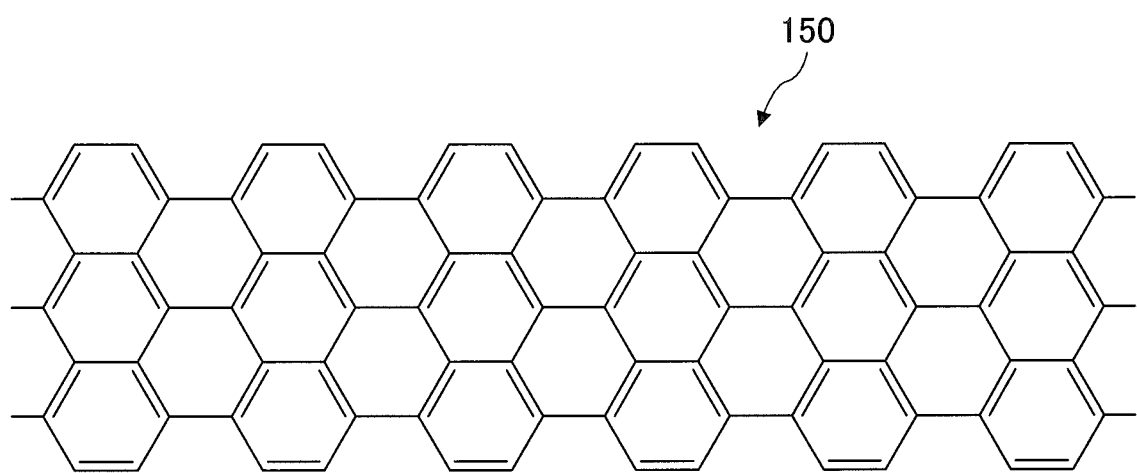
FIG. 3 is a diagram illustrating the hydrogen-terminated GNR.

As illustrated in FIG. 2B, the hydrogen-terminated GNR 150 illustrated in FIG. 3 exhibits properties of an intrinsic (i-type) semiconductor, and the band gap thereof is 1.6 eV. On the other hand, as illustrated in FIG. 2A, the GNR 100 exhibits properties of the intrinsic (i-type) semiconductor, and the band gap thereof is 0.5 eV which is less than ⅓ the band gap of the hydrogen-terminated GNR 150. Hence, the GNR 100 has electron states different from those of the hydrogen-terminated GNR 150, and can contribute to producing various electron states. Further, the GNR 100 has good application properties with respect to various semiconductor devices.

Figure 4A:
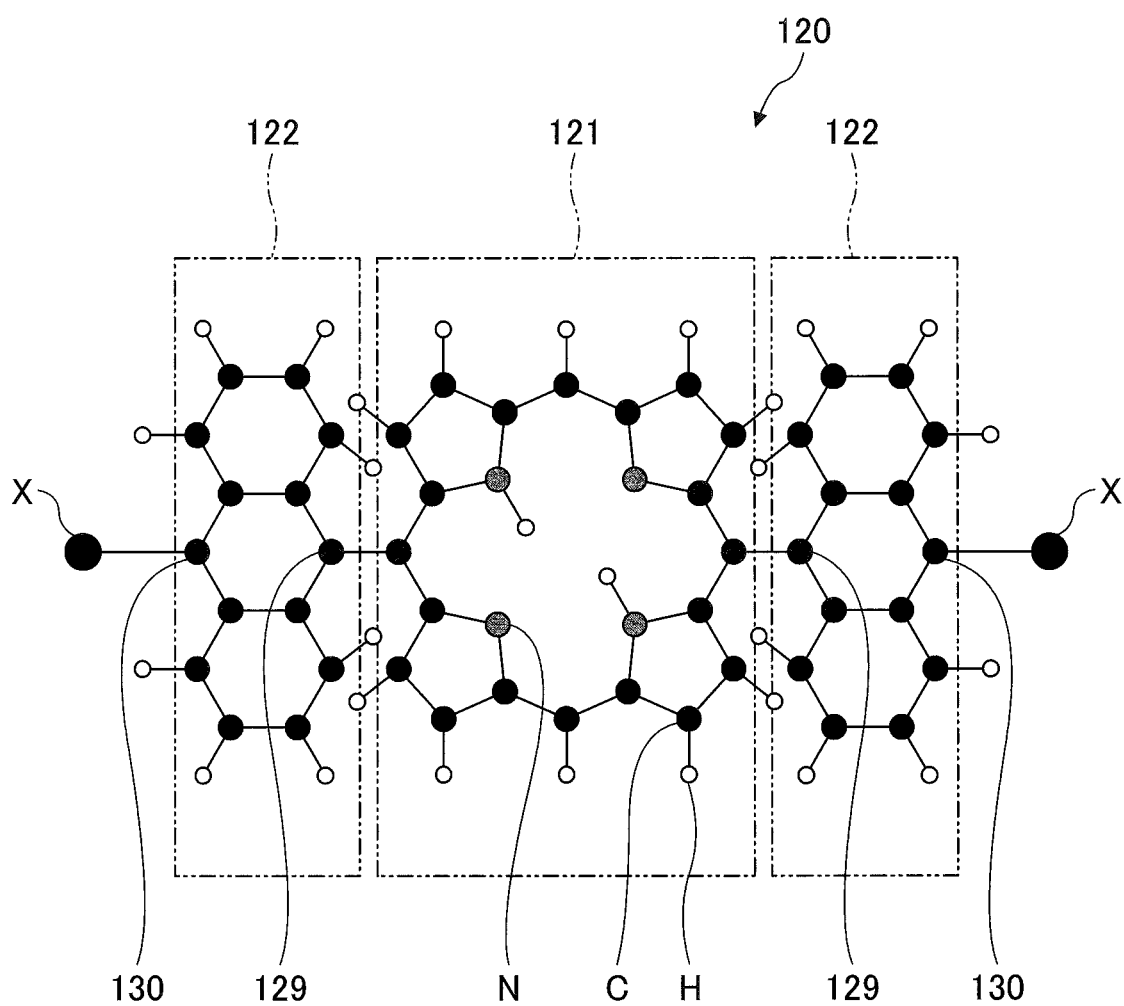
FIG. 4A is a diagram for explaining a method of manufacturing the GNR according to the first embodiment.
Figure 4B:
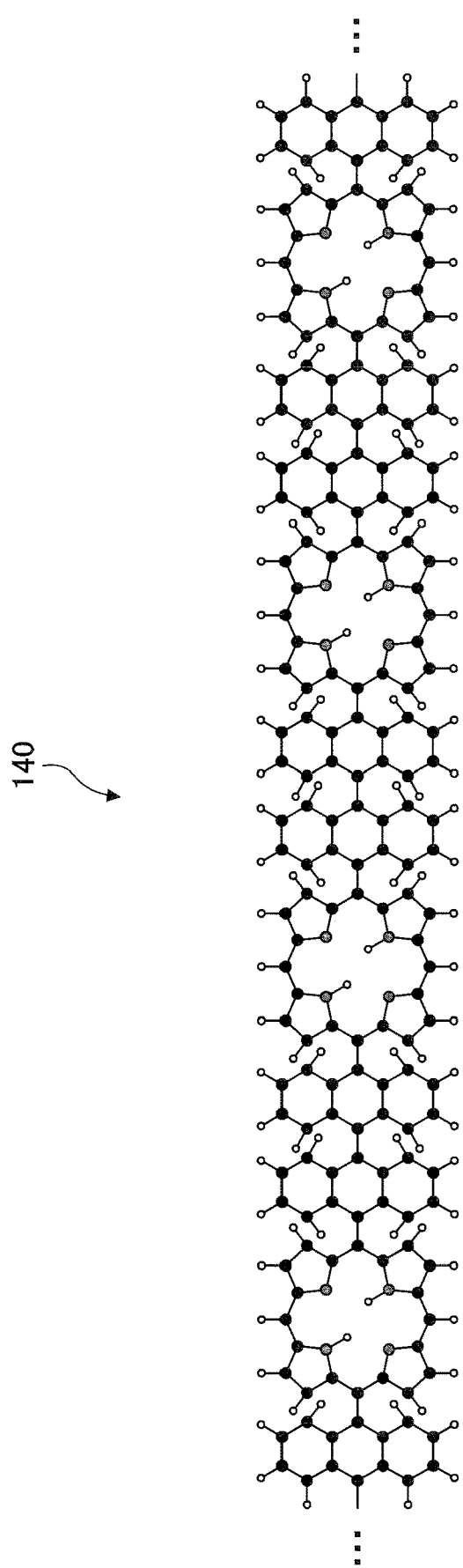
FIG. 4B is a diagram for explaining the method of manufacturing the GNR according to the first embodiment.

Next, a method of manufacturing the GNR 100 will be described. FIG. 4A and FIG. 4B are diagrams illustrating, in sequence, processes of the method of manufacturing the GNR 100.

First, a precursor molecule 120 illustrated in FIG. 4A is prepared. The precursor molecule 120 is represented by the following structural formula (1'). In the precursor molecule 120, X denotes a halogen atom, such as a bromine (Br) atom, for example, that is bonded to a tenth carbon atom 130 of anthracene 122. A ninth carbon atom 129 of the anthracene 122 is bonded to a porphine ring 121.

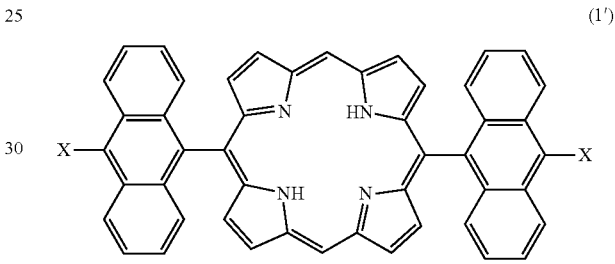

(1')

Then, the precursor molecules 120 are deposited on a (111) face of a heated catalyst metal substrate by vacuum deposition. A substrate made of gold (Au), silver (Ag), copper (Cu), or the like may be used for the catalyst metal substrate. The precursor molecules 120 may be deposited on a (110) face or a (100) face of the catalyst metal substrate by vacuum deposition, or may be deposited on a crystal face of a higher index, such as a (788) face or the like, by vacuum deposition. When using a (111) face of the Au substrate (hereinafter also referred to as the "Au(111) face") as a depositing surface, the temperature of the Au(111) face, cleaned in ultra-high vacuum, is maintained to approximately 200° C. to approximately 300° C., for example, and the precursor molecules 120 are deposited by the vacuum deposition. The amount that is deposited in this state is preferably adjusted to become approximately 1 molecular layer. In this temperature range, a dehalogenation reaction is generated in which desorption of hydrogen bromide (HBr) occurs between the precursor molecules 120 adsorbed on the Au (111) face, to promote polymerization of the precursor molecules 120 (or precursor molecule group). As a result, a polymer 140 illustrated in FIG. 4B is formed.

Thereafter, the Au (111) face having the polymer 140 formed thereon is heated under vacuum to a high temperature of approximately 350° C. to approximately 450° C., for example. In this high temperature range, a dehydrocyclization reaction is generated in which desorption of hydrogen ($H_2$) occurs within the precursor molecules 120 and between the precursor molecules 120 in the polymer 140, to promote aromatization. As a result, the GNR 100 according to the first embodiment is formed.

Hence, the GNR 100 according to the first embodiment can be manufactured by the bottom-up synthesis.

Figure 5:
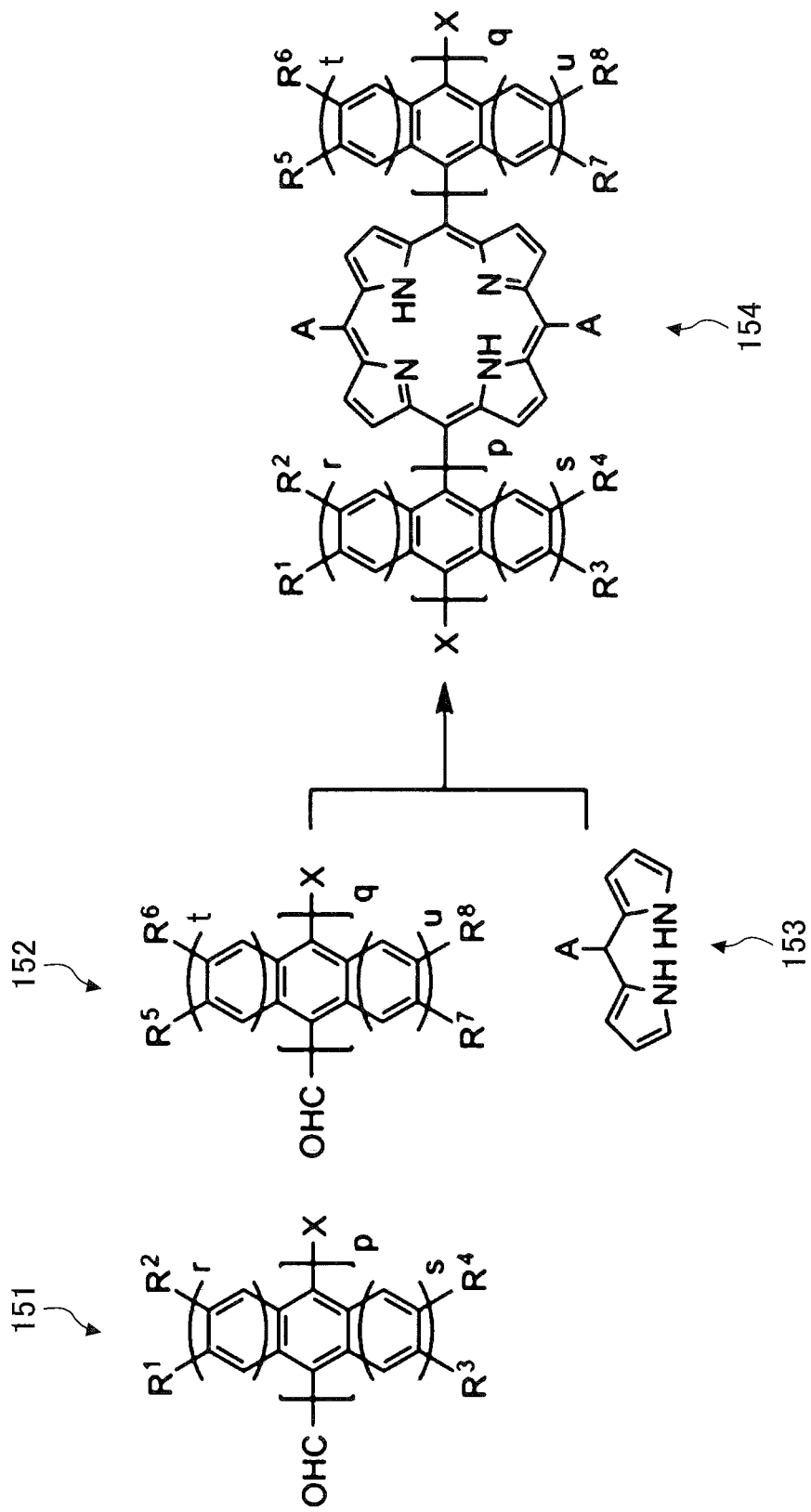
FIG. 5 is a diagram illustrating a method of manufacturing precursor molecules used for manufacturing the GNR according to the first embodiment.

Next, a method of manufacturing the precursor molecules 120 will be described. FIG. 5 is a diagram illustrating the method of manufacturing the precursor molecules used for manufacturing the GNR. First, in this manufacturing method, aryl groups 151 and 152 respectively including halogen moieties and formyl groups, and 2,2'-dipyrromethane 153, are stirred in an organic solvent, and an acid is thereafter added to generate a condensation reaction. Next, an oxidizing agent (or oxidant) is added, and stirred at room temperature or stirred while applying heat, to advance oxidation. As a result, porphyrin 154 is obtained.

In FIG. 5, X denotes a halogen atom, p, q, r, s, t, and u are mutually independent and are integers greater than or equal to 1, $R^1$, $R^2$, $R^3$, $R^4$, $R^5$, $R^6$, $R^7$, and $R^8$ are mutually independent and are one of a hydrogen atom, a substituent, an alkyl moiety, a phenyl moiety, and a halogen atom, and A denotes a hydrogen atom or an aryl group. The integers p, q, r, s, t, and u may be mutually different or, 2 or more integers among these integers p, q, r, s, t, and u may be the same. The $R^1$, $R^2$, $R^3$, $R^4$, $R^5$, $R^6$, $R^7$, and $R^8$ may be mutually different or, 2 or more among these $R^1$, $R^2$, $R^3$, $R^4$, $R^5$, $R^6$, $R^7$, and $R^8$ may be the same. The alkyl moiety and the phenyl moiety among the $R^1$, $R^2$, $R^3$, $R^4$, $R^5$, $R^6$, $R^7$, and $R^8$ may include a substituent. The alkyl moiety may be straight-chained or branch-chained. The carbon number of the alkyl moiety may be 1 to 20, for example. Examples of the alkyl moiety include a methyl group, an ethyl group, a propyl group, an isopropyl group, a butyl group, an isobutyl group, a sec-butyl group, and a tert-butyl group, for example. Examples of the substituent include a hydroxyl group, a nitro group, an amino group, a formyl group, a carboxyl group, and a sulfonyl group, for example. Examples of the halogen atom include a fluorine atom, a chlorine atom, a bromine atom, and an iodine atom, for example. The aryl group A may include a substituent.

Examples of the organic solvent that may be used include a mixture of a halogen-based solvent, such as dichloromethane, chloroform, or the like, that is added with an acid catalyst, for example. Examples of the acid catalyst that may be used include chloranil, trifluoroacetate, propionic acid, 2,3-dichloro-5,6-dicyano-p-benzoquinone, or the like, for example. Examples of the acid that may be used include trifluoroacetate, boron trifluoride-diethyl ether complex, and propionic acid, for example. Examples of the oxidizing agent that may be used include chloranil or 2,3-dichloro-5,6-dicyano-p-benzoquinone, or the like, for example.

When manufacturing the precursor molecule 120, compounds in which each of the integers p, q, r, s, t, and u is 1, and each of the $R^1$, $R^2$, $R^3$, $R^4$, $R^5$, $R^6$, $R^7$, and $R^8$ is H in the above-mentioned structural formulas (3) and (4), may be used for the aryl groups 151 and 152. In other words, the aryl groups 151 and 152 may be represented by the following structural formula (3'). In addition, a compound in which the aryl group A is H may be used for the 2,2-dipyrromethane 153. In other words, the 2,2-dipyrromethane 153 may be represented by the following structural formula (5').

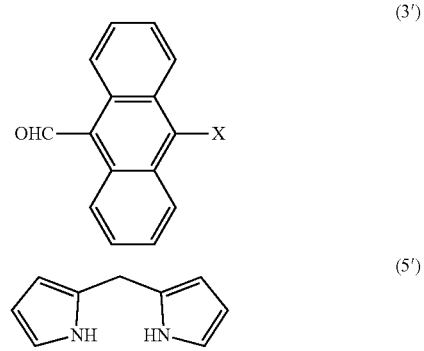

In the following description, a GNR in which the structures represented by the above-mentioned structural formula (11) are arranged, may also be referred to as a porphyrin GNR.

In the above-mentioned structural formulas (9), (3), (4), and (11), the integers p, q, r, s, t, and u may be mutually independent and be integers greater than or equal to 2, the $R^1$, $R^2$, $R^3$, $R^4$, $R^5$, $R^6$, $R^7$, and $R^8$ may be mutually independent and be any one of a substituent, an alkyl moiety, a phenyl moiety, and a halogen atom, and the alkyl group A may be an aryl group.

Second Embodiment

Next, a second embodiment will be described. The second embodiment relates to the GNR. FIG. 6 is a diagram illustrating the GNR according to the second embodiment.

A GNR 200 according to the second embodiment has a structure in which sub-units 213, each including 2 rows of anthracene 212 bonded to a porphine ring 211 that includes a metal atom $M_1$, are arranged as illustrated in FIG. 6. In other words, the GNR 200 has a structure in which each of the integers p, q, r, s, t, and u is 1, each of the $R^1$, $R^2$, $R^3$, $R^4$, $R^5$, $R^6$, $R^7$, and $R^8$ is hydrogen (H), and the alkyl group A is H in the above-mentioned structural formula (8). The metal atom $M_1$ is an atom of magnesium (Mg), iron (Fe), cobalt (Co), nickel (Ni), titanium (Ti), copper (Cu), zinc (Zn), or the like, for example. The metal atom $M_1$ is not limited to the atom of these elements, as long as the metal atom $M_1$ can be coordinated in a porphyrin ring. The GNR 200 includes a chemical structure of a metallic complex of porphyrin.

Figure 7A:
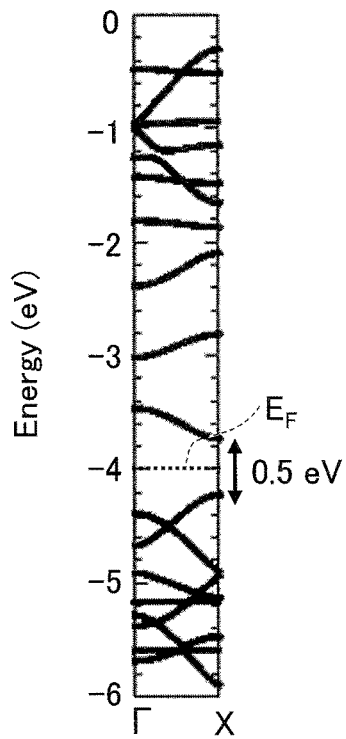
FIG. 7A is a diagram illustrating a band structure (M=Zn) of the GNR according to the second embodiment.
Figure 7B:
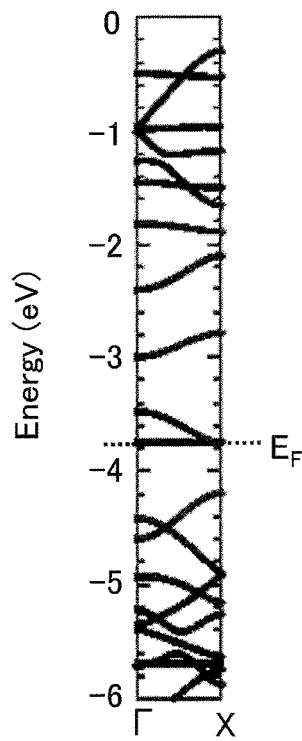
FIG. 7B is a diagram illustrating a band structure (M=Cu) of the GNR according to the second embodiment.
Figure 7C:
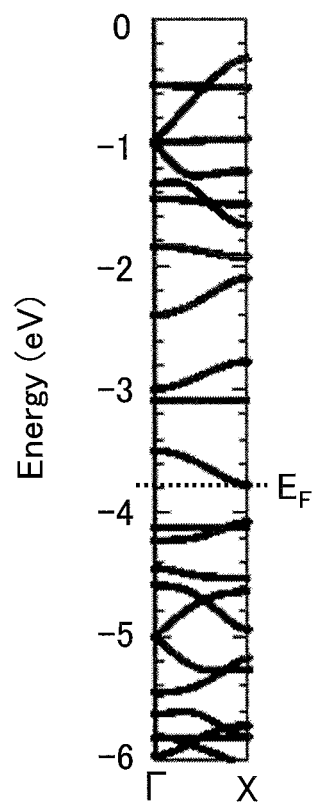
FIG. 7C is a diagram illustrating a band structure (M=Ni) of the GNR according to the second embodiment.

Next, a band structure of the GNR 200 will be described. FIG. 7A through 7C are diagrams illustrating band structures of GNRs predicted according to computations employing the first principle. FIG. 7A illustrates the band structure of the GNR 200 for a case where the metal atom $M_1$ is the Zn atom, FIG. 7B illustrates the band structure of the GNR 200 for a case where the metal atom $M_1$ is the Cu atom, and FIG. 7C illustrates the band structure of the GNR 200 for a case where the metal atom $M_1$ is the Ni atom.

As illustrated in FIG. 7A, in the case where the metal atom $M_1$ is the Zn atom, the GNR 200 exhibits properties of the intrinsic (i-type) semiconductor, and the band gap thereof is 0.5 eV which is less than ⅓ the band gap (1.6 eV) of the hydrogen-terminated GNR 150. As illustrated in FIG. 7B and FIG. 7C, in the cases where the metal atom $M_1$ is the Cu atom and the Ni atom, respectively, a Fermi level $E_F$ is higher than a bottom of a valence band thereof, and the GNRs 200 exhibit properties of an n-type semiconductor. Hence, the GNR 200 has electron states different from those of the hydrogen-terminated GNR 150, and different conductivity types and band gaps are obtained according to the kind of metal used for the metal atom $M_1$. Accordingly, the GNR 200 can contribute to producing various electron states, and the GNR 200 has good application properties with respect to various semiconductor devices.

Figure 8A:
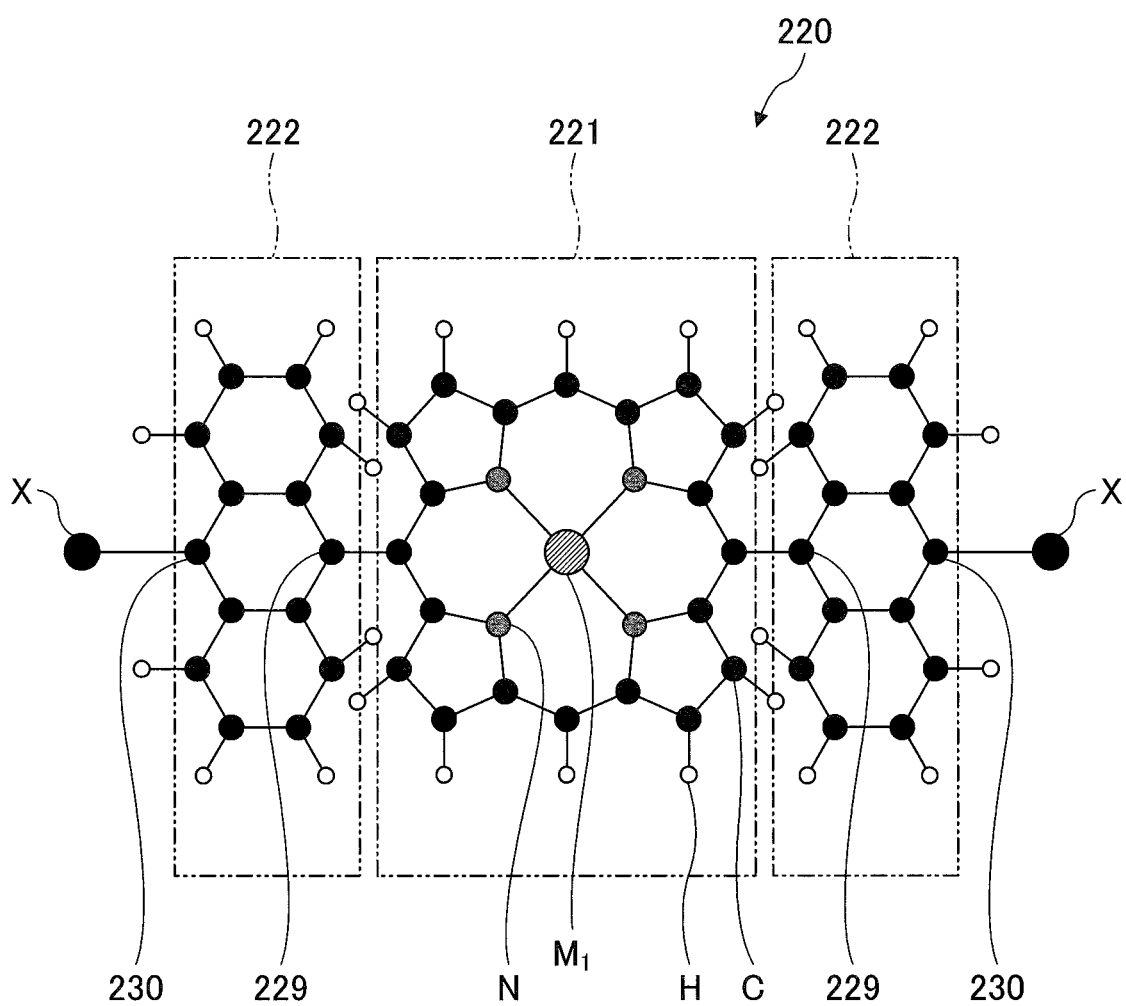
FIG. 8A is a diagram illustrating the method of manufacturing the GNR according to the second embodiment.
Figure 8B:
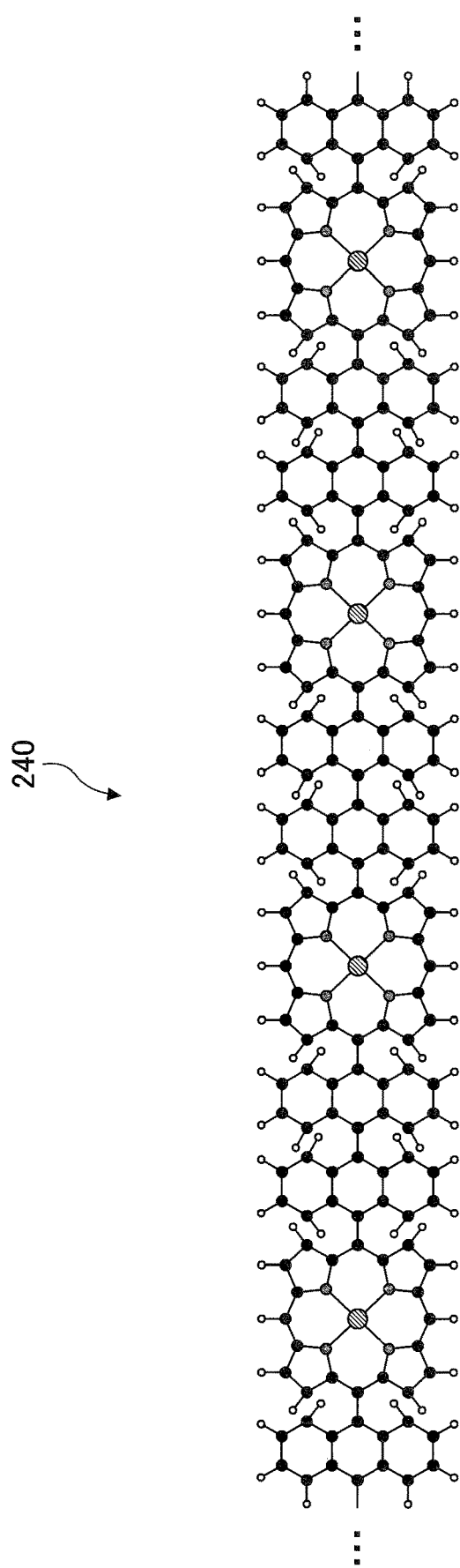
FIG. 8B is a diagram illustrating the method of manufacturing the GNR according to the second embodiment.

Next, a method of manufacturing the GNR 200 will be described. FIG. 8A and FIG. 8B are diagrams illustrating, in sequence, processes of the method of manufacturing the GNR 200.

First, a precursor molecule 220 illustrated in FIG. 8A is prepared. The precursor molecule 220 is represented by the following structural formula (2'). In the precursor molecule 220, X denotes a halogen atom, such as a Br atom, for example, that is bonded to a tenth carbon atom 230 of anthracene 222. A ninth carbon atom 229 of the anthracene 222 is bonded to a porphine ring 221. In addition, the metal atom $M_1$ is bonded to a nitrogen (N) atom of the porphine ring 221. In other words, the precursor molecule 220 is a metal complex. The metal atom $M_1$ may be the atom of Mg, Fe, Co, Ni, Ti, Cu, Zn, or the like, for example.

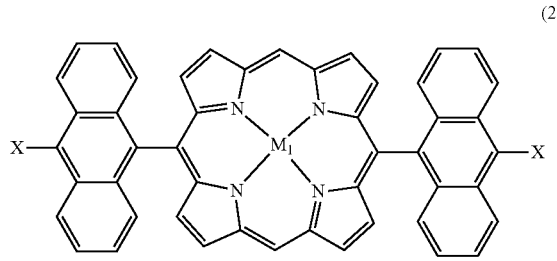

(2')

Next, the precursor molecules 220 are deposited on the (111) face of the heated catalyst metal substrate by vacuum deposition. A substrate made of Au, Ag, Cu, or the like may be used for the catalyst metal substrate. The precursor molecules 220 may be deposited on the (110) face or the (100) face of the catalyst metal substrate by vacuum deposition, or may be deposited on the crystal face of a higher index, such as the (788) face or the like, by vacuum deposition. When using the Au(111) face as the depositing surface, the temperature of the Au(111) face, cleaned in ultra-high vacuum, is maintained to approximately 200° C. to approximately 300° C., for example, and the precursor molecules 220 are deposited by the vacuum deposition. The amount that is deposited in this state is preferably adjusted to become approximately 1 molecular layer. In this temperature range, a dehalogenation reaction is generated in which the desorption of HBr occurs between the precursor molecules 220 adsorbed on the Au(111) face, to promote polymerization of the precursor molecules 220 (or precursor molecule group). As a result, a polymer 240 illustrated in FIG. 8B is formed.

Thereafter, the Au(111) face having the polymer 240 formed thereon is heated under vacuum to a high temperature of approximately 350° C. to approximately 450° C., for example. In this high temperature range, a dehydrocyclization reaction is generated in which desorption of $H_2$ occurs within the precursor molecules 220 and between the precursor molecules 220 in the polymer 240, to promote aromatization. As a result, the GNR 200 according to the second embodiment is formed.

Hence, the GNR 200 according to the second embodiment can be manufactured by the bottom-up synthesis.

Figure 9:
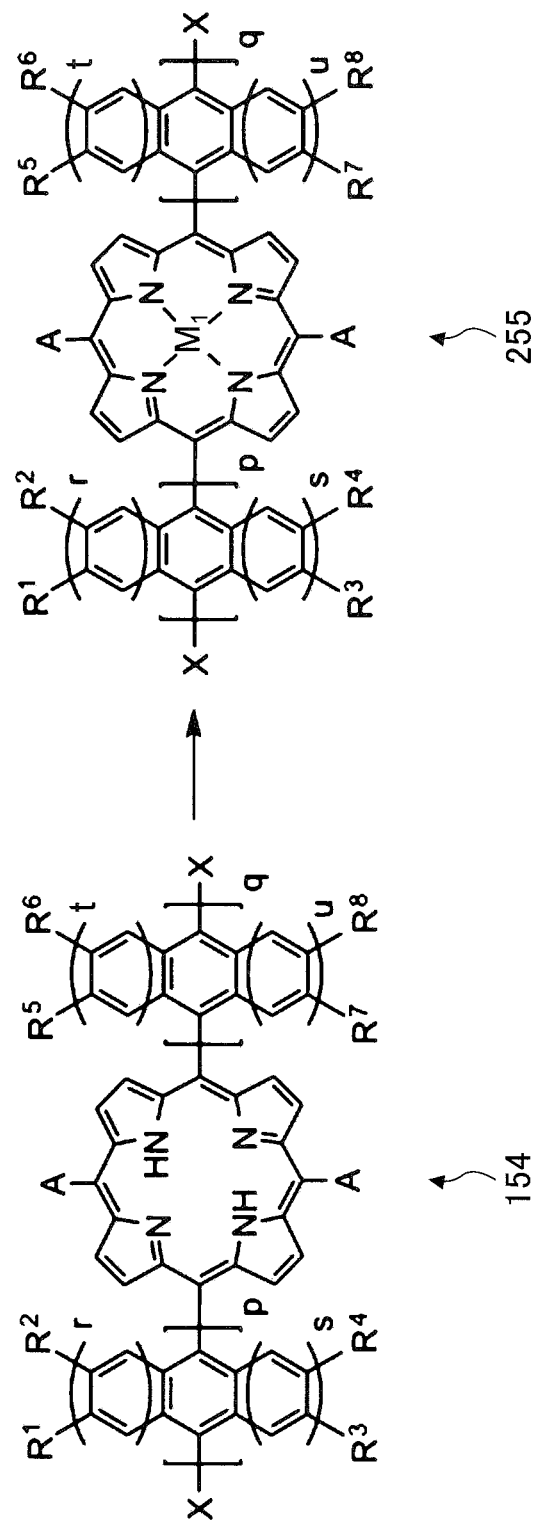
FIG. 9 is a diagram illustrating the method of manufacturing the precursor molecules used for manufacturing the GNR according to the second embodiment.

Next, a method of manufacturing the precursor molecules 220 will be described. FIG. 9 is a diagram illustrating the method of manufacturing the precursor molecules used for manufacturing the GNR. First, in this manufacturing method, the porphyrin 154 is prepared according to the method of manufacturing the precursor molecules described above in conjunction with FIG. 5. Next, the porphyrin 154 and a metallic salt of the metal atom $M_1$ are stirred in an organic solvent. As a result, the metal atom $M_1$ bonds to the N atom of the porphyrin 154, and a porphyrin metal complex 255 is obtained. The stirring in the organic solvent may be performed at room temperature or while applying heat.

Examples of the organic solvent that may be used include N,N-dimethylformamide, dimethyl sulfoxide, acetic acid, pyridine, mixed solvent of dichloromethane-methanol, mixed solvent of chloroform-methanol, or the like, for example.

Examples of salts that may be used for the metallic salt include salts of aluminum (Al), silicon (Si), phosphorus (P), scandium (Sc), titanium (Ti), chromium (Cr), manganese (Mn), iron (Fe), cobalt (Co), nickel (Ni), zinc (Zn), gallium (Ga), germanium (Ge), arsenic (As), yttrium (Y), zirconium (Zr), molybdenum (Mo), ruthenium (Ru), rhodium (Rh), indium (In), palladium (Pd), platinum (Pt), tin (Sn), antimony (Sb), hafnium (Hf), tantalum (Ta), tungsten (W), osmium (Os), iridium (Ir), thallium (Tl), or the like, for example. More particularly, zinc acetate, zinc nitrate, zinc sulfate, zing chloride, or the like may be used when manufacturing the precursor molecule of Zn using the metal atom $M_1$. In addition, copper (II) acetate, copper (II) nitrate, copper (II) sulfate, copper (II) chloride, or the like may be used when manufacturing the precursor molecule of Cu using the metal atom $M_1$. Further, nickel acetate, nickel nitrate, nickel sulfate, nickel chloride, or the like may be used when manufacturing the precursor molecule of Ni using the metal atom $M_1$. Titanocene dichloride, titanium oxide bisacetylacetonate, or the like may be used when manufacturing the precursor molecule of Ti using the metal atom $M_1$. However, when using titanium oxide bis acetylacetonate, the metal atom $M_1$ becomes an oxide of Ti (TiO), and not Ti itself. Iron acetate, iron sulfate, iron chloride, or the like may be used when manufacturing the precursor molecule of Fe using the metal atom $M_1$. Magnesium acetate, magnesium nitrate, magnesium sulfate, magnesium chloride, or the like may be used when manufacturing the precursor molecule of Mg using the metal atom $M_1$. However, the metallic salt is of course not limited to salts described above.

When manufacturing the precursor molecule 220, the porphyrin 154 in which each of the integers p, q, r, s, t, and u is 1, each of the $R^1$, $R^2$, $R^3$, $R^4$, $R^5$, $R^6$, $R^7$, and $R^8$ is H, and the alkyl group A is H.

In the following description, the GNR in which structures represented by the above-mentioned structural formula (10) are arranged, may also be referred to as a porphyrin metal complex GNR.

In the above-mentioned structural formulas (8) and (10), the integers p, q, r, s, t, and u may be mutually independent and be integers greater than or equal to 2, the $R^1$, $R^2$, $R^3$, $R^4$, $R^5$, $R^6$, $R^7$, and $R^8$ may be mutually independent and be any one of a substituent, an alkyl moiety, a phenyl moiety, and a halogen atom, and the alkyl group A may be an aryl group.

Third Embodiment

Figure 10:
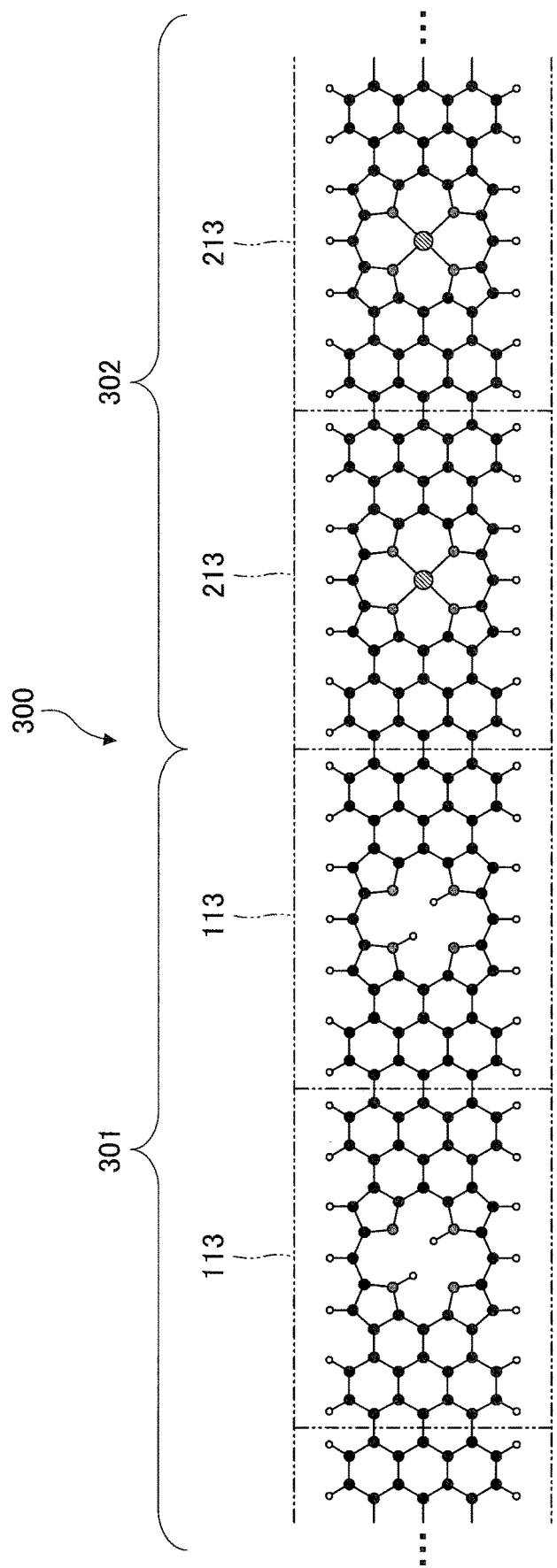
FIG. 10 is a diagram illustrating the GNR according to a third embodiment.

Next, a third embodiment will be described. The third embodiment relates to the GNR. FIG. 10 is a diagram illustrating the GNR according to the third embodiment.

A GNR 300 according to the third embodiment includes a porphyrin GNR part 301, and a porphyrin metal complex GNR part 302, as illustrated in FIG. 10. The porphyrin GNR part 301 includes a structure in which a plurality of sub-units 113 are arranged. In other words, the porphyrin GNR part 301 has a structure in which h is an integer greater than or equal to 1, each of the integers p, q, r, s, t, and u is 1, each of the $R^1$, $R^2$, $R^3$, $R^4$, $R^5$, $R^6$, $R^7$, and $R^8$ is H, and the alkyl group A is H in the following structural formula (14). The porphyrin metal complex GNR part 302 includes a structure in which a plurality of sub-units 213 are arranged. In other words, the porphyrin metal complex GNR part 302 has a structure in which g is an integer greater than or equal to 1, each of the integers p, q, r, s, t, and u is 1, each of the $R^1$, $R^2$, $R^3$, $R^4$, $R^5$, $R^6$, $R^7$, and $R^8$ is H, and the alkyl group A is H in the following structural formula (13). The sub-unit 213 includes, in a part thereof, the structure presented by the above-mentioned structural formula (10). The sub-unit 113 includes, in a part thereof, the structure presented by the above-mentioned structural formula (11). The porphyrin metal complex GNR part 302 is an example of a first unit, and the porphyrin GNR part 301 is an example of a second unit. The porphyrin GNR part 301 and the porphyrin metal complex GNR part 302 are bonded to each other by a carbon-to-carbon bonding at respective ends of the porphyrin GNR part 301 and the porphyrin metal complex GNR part 302. The GNR 300 includes the chemical structure of porphyrin and the chemical structure of the metal complex of porphyrin.

According to the third embodiment, it is possible to form a heterojunction between the porphyrin GNR part 301 and the porphyrin metal complex GNR part 302 that have different electron states. Hence, the GNR 300 can contribute to producing various electron states, and the GNR 300 has good application properties with respect to various semiconductor devices.

Figure 11A:
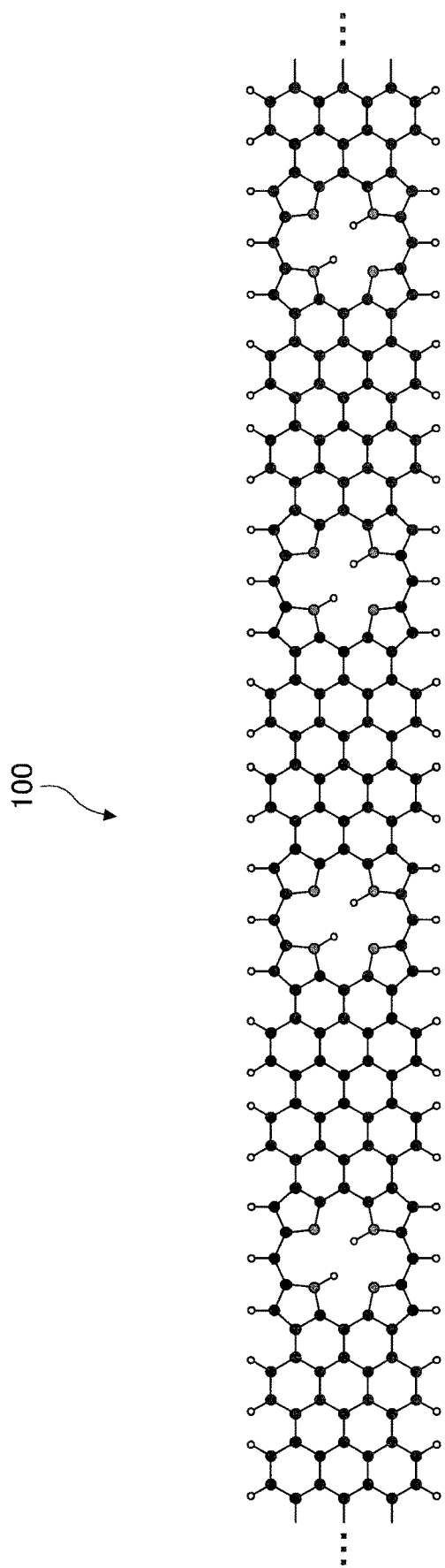
FIG. 11A is a diagram illustrating the method of manufacturing the GNR according to the third embodiment.
Figure 11B:
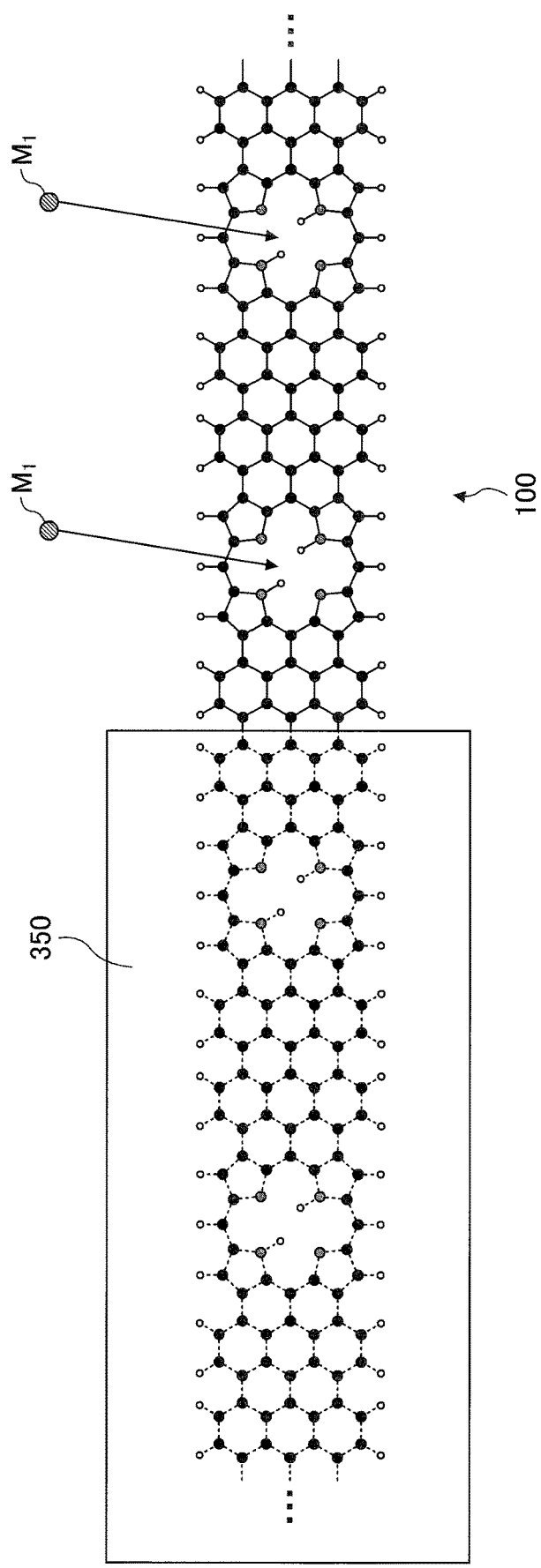
FIG. 11B is a diagram illustrating the method of manufacturing the GNR according to the third embodiment.

Next, a method of manufacturing the GNR 300 will be described. FIG. 11A and FIG. 11B are diagrams illustrating, in sequence, processes of the method of manufacturing the GNR 300.

First, as illustrated in FIG. 11A, the GNR 100 according to the first embodiment is formed on the catalyst metal substrate. Next, as illustrated in FIG. 11B, a mask 350, that exposes a region where the porphyrin metal complex GNR part 302 of the GNR 100 is to be formed, and covers the remaining region, is formed on the GNR 100. Thereafter, the GNR 100 having the mask 350 formed thereon, is immersed into an organic solvent having dissolved therein the metallic salt of the metal atom $M_1$ to be included in the porphyrin metal complex GNR part 302, together with the catalyst metal substrate, and the organic solvent is stirred. As a result, the metal atom $M_1$ bonds to the N atom of the porphine ring 111, to form the porphyrin metal complex GNR part 302, at the region of the GNR 100 exposed from the mask 350. In addition, the remaining region of the GNR 100 becomes the porphyrin GNR part 301. The organic solvent may be stirred at room temperature, or may be stirred while applying heat. Then, the catalyst metal substrate is extracted from the

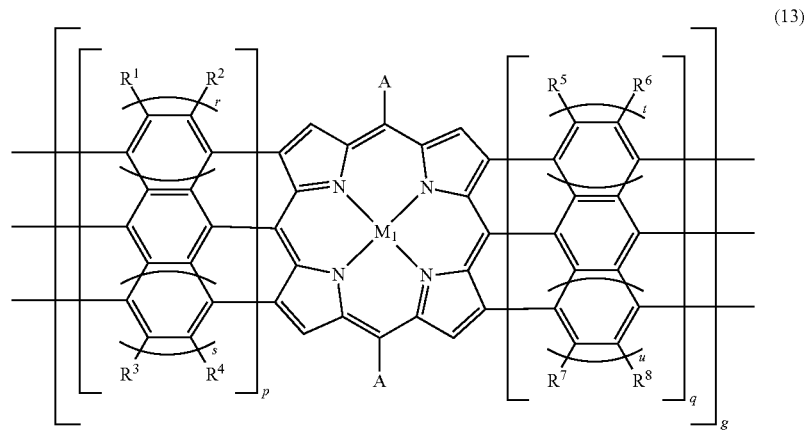

(13)

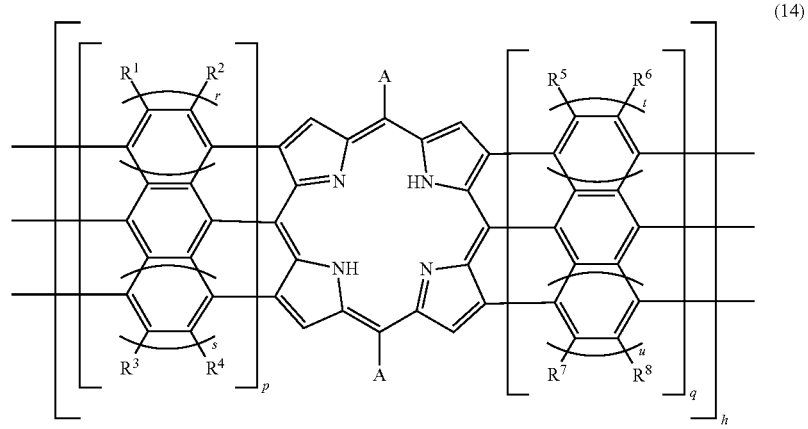

(14)

organic solvent, together with the porphyrin GNR part 301 and the porphyrin metal complex GNR part 302, and the mask 350 is removed.

Hence, the GNR 300 according to the third embodiment can be manufactured by the processes described heretofore.

For example, a metallic salt similar to the metallic salt used by the method of manufacturing the precursor molecule described above in conjunction with FIG. 9, may be used for the metallic salt of the metal atom $M_1$ included in the porphyrin metal complex GNR part 302. A material forming the mask 350 is not particularly limited, and the kind of organic solvent used is not particularly limited. Preferably, the material used for the mask 350 is polymethyl methacrylate (PMMA), and the kind of organic solvent used is an aqueous solution of acetic acid.

According to the third embodiment, the porphyrin metal complex GNR part 302 and the porphyrin GNR part 301 have structures in which each of the integers p, q, r, s, t, and u is 1, each of the $R^1$, $R^2$, $R^3$, $R^4$, $R^5$, $R^6$, $R^7$, and $R^8$ is H, and the alkyl group A is H in the above-mentioned structural formulas (13) and (14), respectively. However, in the above-mentioned structural formulas (13) and (14), the integers p, q, r, s, t, and u may be mutually independent and be integers greater than or equal to 2, the $R^1$, $R^2$, $R^3$, $R^4$, $R^5$, $R^6$, $R^7$, and $R^8$ may be mutually independent and be any one of a substituent, an alkyl moiety, a phenyl moiety, and a halogen atom, and the alkyl group A may be an aryl group. The porphyrin metal complex GNR part 302 and the porphyrin GNR part 301 may be arranged periodically.

Fourth Embodiment

Figure 12:
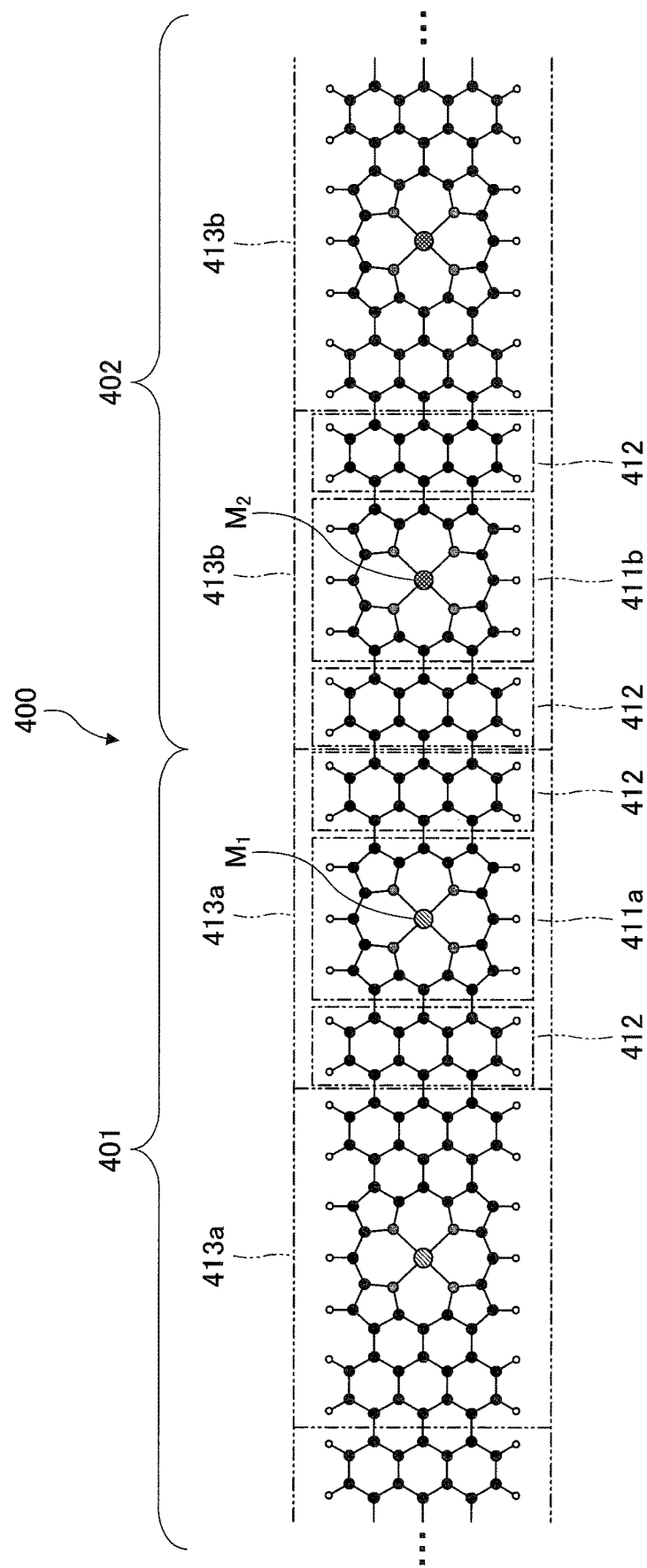
FIG. 12 is a diagram illustrating the GNR according to a fourth embodiment.

Next, a fourth embodiment will be described. The fourth embodiment relates to the GNR. FIG. 12 is a diagram illustrating the GNR according to the fourth embodiment.

A GNR 400 according to the fourth embodiment includes a porphyrin metal complex GNR part 401, and a porphyrin metal complex GNR part 402, as illustrated in FIG. 12. The porphyrin metal complex GNR part 401 includes a structure in which a plurality of sub-units 413a, each including 2 rows of anthracene 412 bonded to a porphine ring 411a that includes a metal atom $M_1$, are arranged. In other words, the porphyrin metal complex GNR part 401 has a structure in which g is an integer greater than or equal to 1, each of the integers p, q, r, s, t, and u is 1, each of the $R^1$, $R^2$, $R^3$, $R^4$, $R^5$, $R^6$, $R^7$, and $R^8$ is H, and the alkyl group A is H in the above-mentioned structural formula (13). The porphyrin metal complex GNR part 402 includes a structure in which a plurality of sub-units 413b, each including 2 rows of anthracene 412 bonded to a porphine ring 411b that includes a metal atom $M_2$, are arranged. In other words, the porphyrin metal complex GNR part 402 has a structure in which h is an integer greater than or equal to 1, each of the integers p, q, r, s, t, and u is 1, each of the $R^1$, $R^2$, $R^3$, $R^4$, $R^5$, $R^6$, $R^7$, and $R^8$ is H, and the alkyl group A is H in the above-mentioned structural formula (15). The sub-unit 413a includes, in a part thereof, the structure represented by the above-mentioned structural formula (10). The sub-unit 413b includes, in a part thereof, the structure represented by the above-mentioned structural formula (12). The metal atoms $M_1$ and $M_2$ are selected from Mg, Fe, Co, Ni, Ti, Cu, Zn, or the like, for example, and are mutually different. The metal atoms $M_1$ and $M_2$ are not limited to these elements, as long as the metal atoms $M_1$ and $M_2$ can be coordinated in a porphyrin ring. The porphyrin metal complex GNR part 401 is an example of a first unit, and the porphyrin metal complex GNR part 402 is an example of a second unit. The porphyrin metal complex GNR part 401 and the porphyrin metal complex GNR part 402 are bonded to each other by a carbon-to-carbon bonding at respective ends of the porphyrin metal complex GNR part 401 and the porphyrin metal complex GNR part 402. The GNR 400 includes the chemical structure of the metal complex of porphyrin.

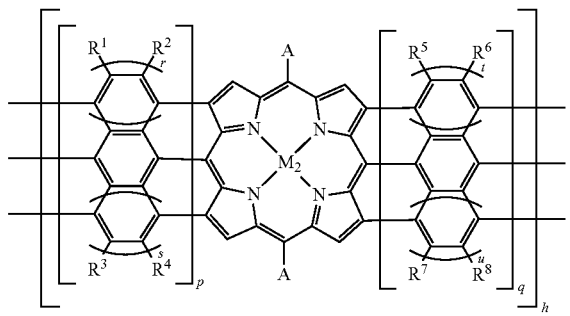

(15)

According to the fourth embodiment, it is possible to form a heterojunction between the porphyrin metal complex GNR part 401 and the porphyrin metal complex GNR part 402. Hence, the GNR 400 can contribute to producing various electron states, and the GNR 400 has good application properties with respect to various semiconductor devices.

Figure 13A:
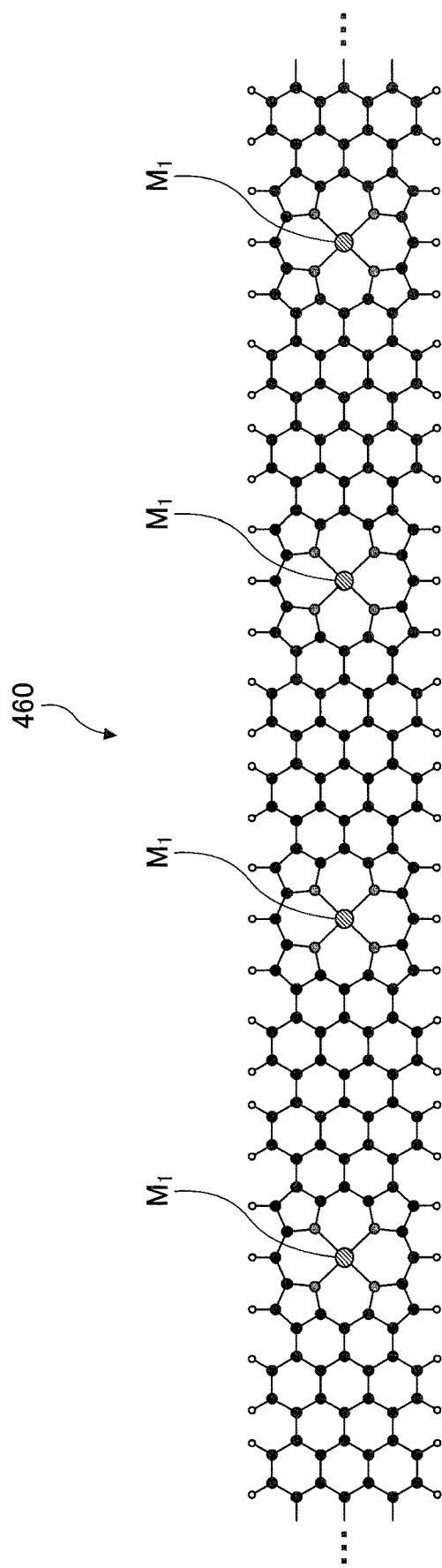
FIG. 13A is a diagram illustrating the method of manufacturing the GNR according to the fourth embodiment.
Figure 13B:
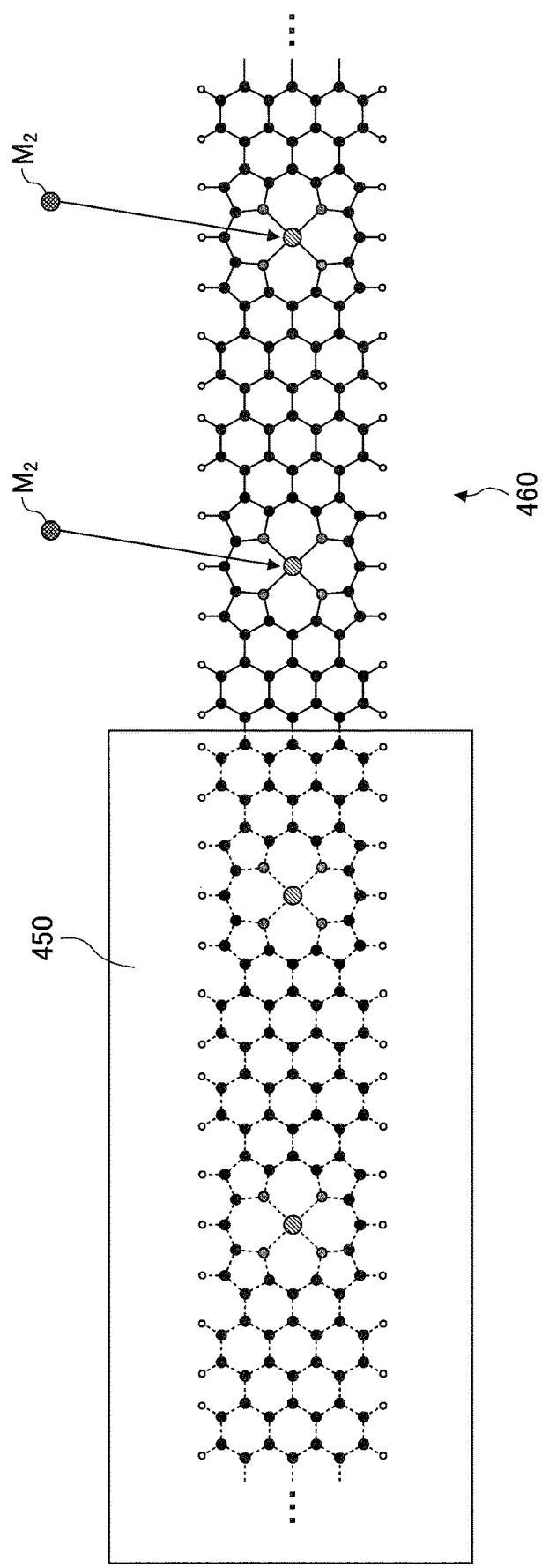
FIG. 13B is a diagram illustrating the method of manufacturing the GNR according to the fourth embodiment.

Next, a method of manufacturing the GNR 400 will be described. FIG. 13A and FIG. 13B are diagrams illustrating, in sequence, processes of the method of manufacturing the GNR 400. In this example, it is assumed for the sake of convenience that the metal atom $M_2$ more easily bonds to the N atom of the porphine ring than the metal atom $M_1$.

First, as illustrated in FIG. 13A, a porphyrin metal complex GNR 460 having the metal atom M1 bonded to the N atom of the porphine ring, is formed on the catalyst metal substrate according to the method of manufacturing the GNR 200. Next, as illustrated in FIG. 13B, a mask 450, that exposes a region where a porphyrin metal complex GNR part 402 of the porphyrin metal complex GNR 460 is to be formed, and covers the remaining region, is formed on the porphyrin metal complex GNR 460. Thereafter, the porphyrin metal complex GNR 460 having the mask 450 formed thereon, is immersed into an organic solvent having dissolved therein the metallic salt of the metal atom $M_2$ to be included in the porphyrin metal complex GNR part 402, together with the catalyst metal substrate, and the organic solvent is stirred. As a result, the metal atom $M_2$ bonds to the N atom in place of the metal atom $M_1$, to form the porphyrin metal complex GNR part 402, at the region of the porphyrin metal complex GNR 460 exposed from the mask 450. In addition, the remaining region of the porphyrin metal complex GNR 460 becomes the porphyrin metal complex GNR part 401. The organic solvent may be stirred at room temperature, or may be stirred while applying heat. Then, the catalyst metal substrate is extracted from the organic solvent, together with the porphyrin metal complex GNR part 401 and the porphyrin metal complex GNR part 402, and the mask 450 is removed.

Hence, the GNR 400 according to the fourth embodiment can be manufactured by the processes described heretofore.

For example, a metallic salt similar to the metallic salt used by the method of manufacturing the precursor molecule described above in conjunction with FIG. 9, may be used for the metallic salt of the metal atom $M_2$ included in the porphyrin metal complex GNR part 402. A material forming the mask 450 is not particularly limited, and the kind of organic solvent used is not particularly limited. Preferably, the material used for the mask 450 is PMMA, and the kind of organic solvent used is an aqueous solution of acetic acid.

In a case where the metal atom $M_1$ more easily bonds to the N atom of the porphine ring than the metal atom $M_2$, a porphyrin metal complex GNR having the metal atom $M_2$ bonded to the porphine ring may be prepared, and a part of the metal atoms $M_2$ may be substituted by the metal atoms $M_1$. In this case, a metallic salt similar to the metallic salt used by the method of manufacturing the precursor molecule described above in conjunction with FIG. 9, may also be used for the metallic salt of the metal atom $M_1$ included in the porphyrin metal complex GNR part 401.

According to the fourth embodiment, the porphyrin metal complex GNR part 401 and the porphyrin metal complex GNR part 402 have structures in which each of the integers p, q, r, s, t, and u is 1, each of the $R^1$, $R^2$, $R^3$, $R^4$, $R^5$, $R^6$, $R^7$, and $R^8$ is H, and the alkyl group A is H in the above-mentioned structural formulas (13) and (15), respectively. However, in the above-mentioned structural formulas (13) and (15), the integers p, q, r, s, t, and u may be mutually independent and be integers greater than or equal to 2, the $R^1$, $R^2$, $R^3$, $R^4$, $R^5$, $R^6$, $R^7$, and $R^8$ may be mutually independent and be any one of a substituent, an alkyl moiety, a phenyl moiety, and a halogen atom, and the alkyl group A may be an aryl group. The porphyrin metal complex GNR part 401 and the porphyrin metal complex GNR part 402 may be arranged periodically.

Fifth Embodiment

Next, a fifth embodiment will be described. The fifth embodiment relates to a nanoribbon including porphyrin as sub-units. FIG. 14 is a diagram illustrating the nanoribbon according to the fifth embodiment.

A nanoribbon 500 according to the fifth embodiment includes a porphyrin nanoribbon part 501, and a porphyrin metal complex nanoribbon part 502, as illustrated in FIG. 14. The porphyrin nanoribbon part 501 includes a structure in which sub-units of a porphine ring 511a are arranged. The porphyrin metal complex nanoribbon part 502 includes a structure in which sub-units of a porphine ring 511b are arranged. A metal atom $M_1$ is bonded to the N atom of the porphine ring 511b. The porphyrin metal complex nanoribbon part 502 is an example of a first unit, and the porphyrin nanoribbon part 501 is an example of a second unit. The porphyrin nanoribbon part 501 and the porphyrin metal complex nanoribbon part 502 are bonded to each other by a carbon-to-carbon bonding at respective ends of the porphyrin nanoribbon part 501 and the porphyrin metal complex nanoribbon part 502. The nanoribbon 500 includes the chemical structure of porphyrin and the chemical structure of the metal complex of porphyrin.

According to the fifth embodiment, it is possible to form a heterojunction between the porphyrin nanoribbon part 501 and the porphyrin metal complex nanoribbon part 502. Hence, the nanoribbon 500 can contribute to producing various electron states, and the nanoribbon 500 has good application properties with respect to various semiconductor devices.

Figure 15A:
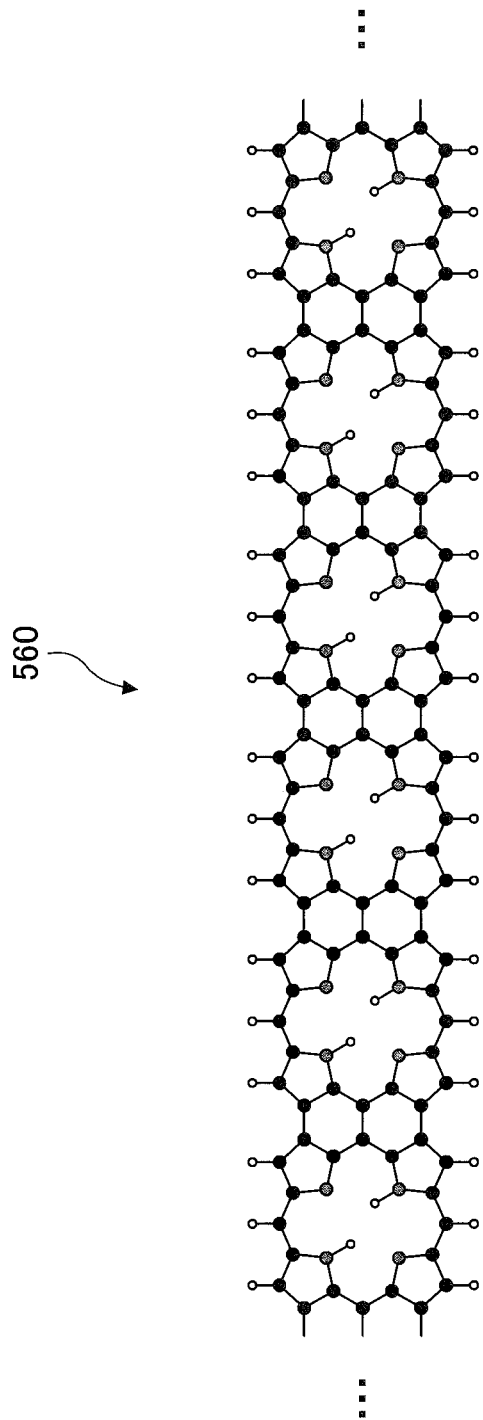
FIG. 15A is a diagram illustrating the method of manufacturing the nanoribbon according to the fifth embodiment.

Next, a method of manufacturing the nanoribbon 500 will be described. FIG. 15A and FIG. 15B are diagrams illustrating, in sequence, processes of the method of manufacturing the nanoribbon 500.

First, as illustrated in FIG. 15A, a porphyrin nanoribbon 560 is formed on a catalyst metal substrate. The porphyrin nanoribbon 560 can be synthesized on the catalyst metal substrate by polymerizing the porphyrin 154 in which each of the integers p, q, r, s, t, and u is 0, and the alkyl group A is H, for example. The porphyrin nanoribbon 560 is described in Akihiko Tsuda et al., "Fully Conjugated Porphyrin Tapes with Electronic Absorption Bands That Reach into Infrared", Science, Vol. 293, 6 Jul. 2001, pp. 79-82, and Tien Quang Nguyen et al., "Adsorption of diatomic molecules on iron tape-porphyrin: A comparative study", Physical Review, B 77, 195307, 2008, pp. 1-7, for example. Next, as illustrated in FIG. 15B, a mask 550, that exposes a region where the porphyrin metal complex nanoribbon part 502 of the porphyrin nanoribbon 560 is to be formed, and covers the remaining region, is formed on the porphyrin nanoribbon 560. Thereafter, the porphyrin nanoribbon 560 having the mask 550 formed thereon, is immersed into an organic solvent having dissolved therein the metallic salt of the metal atom $M_1$ to be included in the porphyrin metal complex nanoribbon part 502, together with the catalyst metal substrate, and the organic solvent is stirred. As a result, the metal atom $M_1$ bonds to the N atom of the porphine ring, to form the porphyrin metal complex nanoribbon part 502, at the region of the porphyrin nanoribbon 560 exposed from the mask 550. In addition, the remaining region of the porphyrin nanoribbon 560 becomes the porphyrin nanoribbon part 501. The organic solvent may be stirred at room temperature, or may be stirred while applying heat. Then, the catalyst metal substrate is extracted from the organic solvent, together with the porphyrin nanoribbon part 501 and the porphyrin metal complex nanoribbon part 502, and the mask 550 is removed.

Hence, the nanoribbon 500 according to the fifth embodiment can be manufactured by the processes described heretofore.

A material forming the mask 550 is not particularly limited, and the kind of organic solvent used is not particularly limited. Preferably, the material used for the mask 550 is PMMA, and the kind of organic solvent used is an aqueous solution of acetic acid.

Sixth Embodiment

Next, a sixth embodiment will be described. The sixth embodiment relates to the nanoribbon including the porphyrin as the sub-units. FIG. 16 is a diagram illustrating the nanoribbon according to the sixth embodiment.

A nanoribbon 600 according to the sixth embodiment includes a porphyrin metal complex nanoribbon part 601, and a porphyrin metal complex nanoribbon part 602, as illustrated in FIG. 16. The porphyrin metal complex nanoribbon part 601 includes a structure in which sub-units of a porphine ring 611a are arranged. The porphyrin metal complex nanoribbon part 602 has a structure in which sub-units of a porphine ring 611b are arranged. A metal atom $M_1$ is bonded to the N atom of the porphine ring 611a, and a metal atom $M_2$ is bonded to the N atom of the porphine ring 611b. The porphyrin metal complex nanoribbon part 601 is an example of a first unit, and the porphyrin metal complex nanoribbon part 602 is an example of a second unit. The porphyrin metal complex nanoribbon part 601 and the porphyrin metal complex nanoribbon part 602 are bonded to each other by a carbon-to-carbon bonding at respective ends of the porphyrin metal complex nanoribbon part 601 and the porphyrin metal complex nanoribbon part 602. The nanoribbon 600 includes the chemical structure of the metal complex of porphyrin.

According to the sixth embodiment, it is possible to form a heterojunction between the porphyrin metal complex nanoribbon part 601 and the porphyrin metal complex nanoribbon part 602. Hence, the nanoribbon 600 can contribute to producing various electron states, and the nanoribbon 600 has good application properties with respect to various semiconductor devices.

Figure 17A:
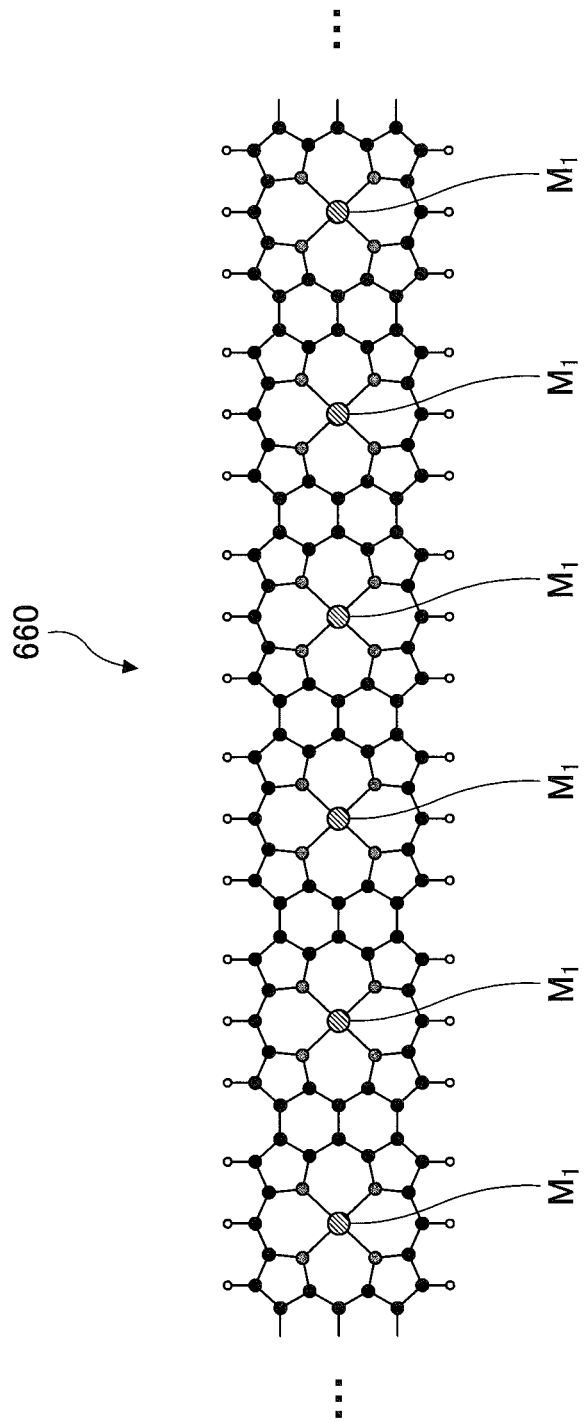
FIG. 17A is a diagram illustrating the method of manufacturing the nanoribbon according to the sixth embodiment.
Figure 17B:
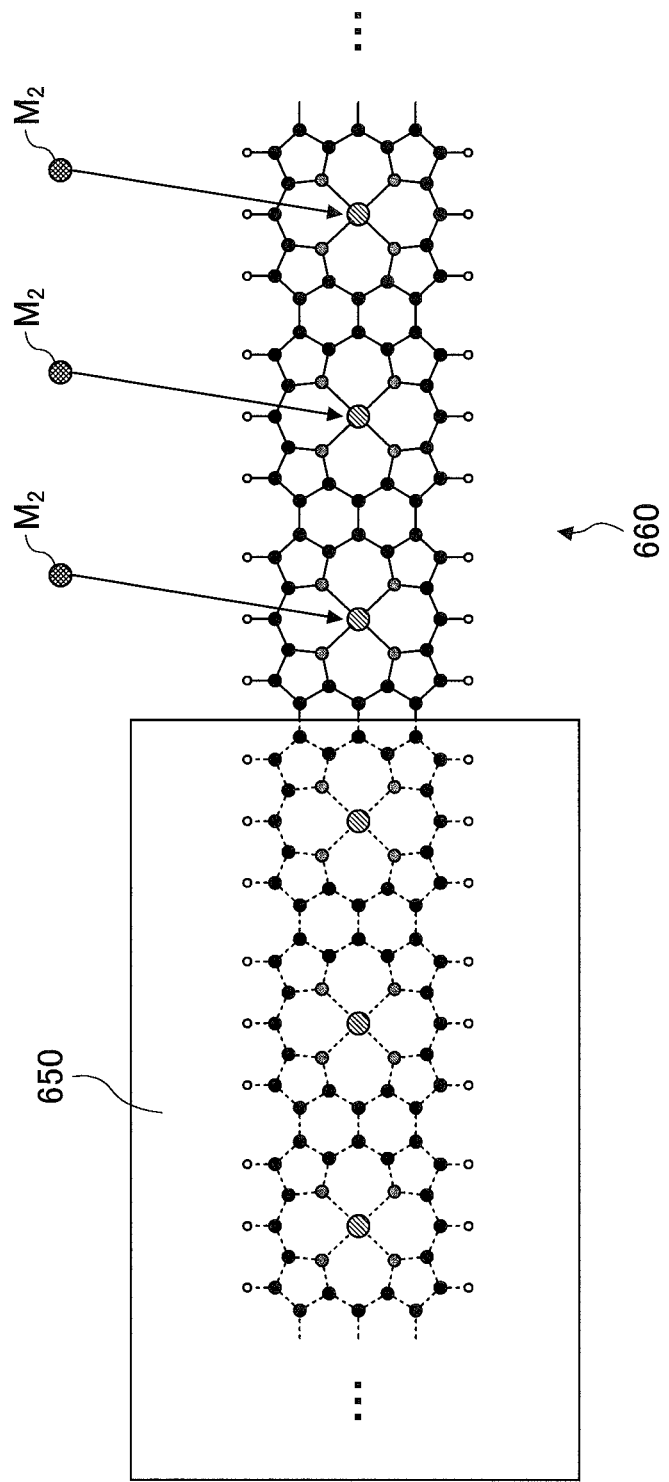
FIG. 17B is a diagram illustrating the method of manufacturing the nanoribbon according to the sixth embodiment.

Next, a method of manufacturing the nanoribbon 600 will be described. FIG. 17A and FIG. 17B are diagrams illustrating, in sequence, processes of the method of manufacturing the nanoribbon 600. In this example, it is assumed for the sake of convenience that the metal atom $M_2$ more easily bonds to the N atom of the porphine ring than the metal atom $M_1$.

First, as illustrated in FIG. 17A, a porphyrin metal complex nanoribbon 660 is formed on a catalyst metal substrate. The porphyrin nanoribbon 660 can be synthesized on the catalyst metal substrate by polymerizing the porphyrin metal complex 255 in which each of the integers p, q, r, s, t, and u is 0, and the alkyl group A is H, for example. Next, as illustrated in FIG. 17B, a mask 650, that exposes a region where a porphyrin metal complex nanoribbon part 602 of the porphyrin metal complex nanoribbon 660 is to be formed, and covers the remaining region, is formed on the porphyrin metal complex nanoribbon 660. Thereafter, the porphyrin metal complex nanoribbon 660 having the mask 650 formed thereon, is immersed into an organic solvent having dissolved therein the metallic salt of the metal atom $M_2$ to be included in the porphyrin metal complex nanoribbon part 602, together with the catalyst metal substrate, and the organic solvent is stirred. As a result, the metal atom $M_2$ bonds to the N atom in place of the metal atom $M_1$, to form the porphyrin metal complex nanoribbon part 602, at the region of the porphyrin metal complex nanoribbon 660 exposed from the mask 650. In addition, the remaining region of the porphyrin metal complex nanoribbon 660 becomes the porphyrin metal complex nanoribbon part 601. The organic solvent may be stirred at room temperature, or may be stirred while applying heat. Then, the catalyst metal substrate is extracted from the organic solvent, together with the porphyrin metal complex nanoribbon part 601 and the porphyrin metal complex nanoribbon part 602, and the mask 650 is removed.

Hence, the nanoribbon 600 according to the sixth embodiment can be manufactured by the processes described heretofore.

A material forming the mask 650 is not particularly limited, and the kind of organic solvent used is not particularly limited. Preferably, the material used for the mask 650 is PMMA, and the kind of organic solvent used is an aqueous solution of acetic acid.

In a case where the metal atom $M_1$ more easily bonds to the N atom of the porphine ring than the metal atom $M_2$, a porphyrin metal complex nanoribbon having the metal atom $M_2$ bonded to the porphine ring may be prepared, and a part of the metal atoms $M_2$ may be substituted by the metal atoms $M_1$.

Seventh Embodiment

Figure 18A:
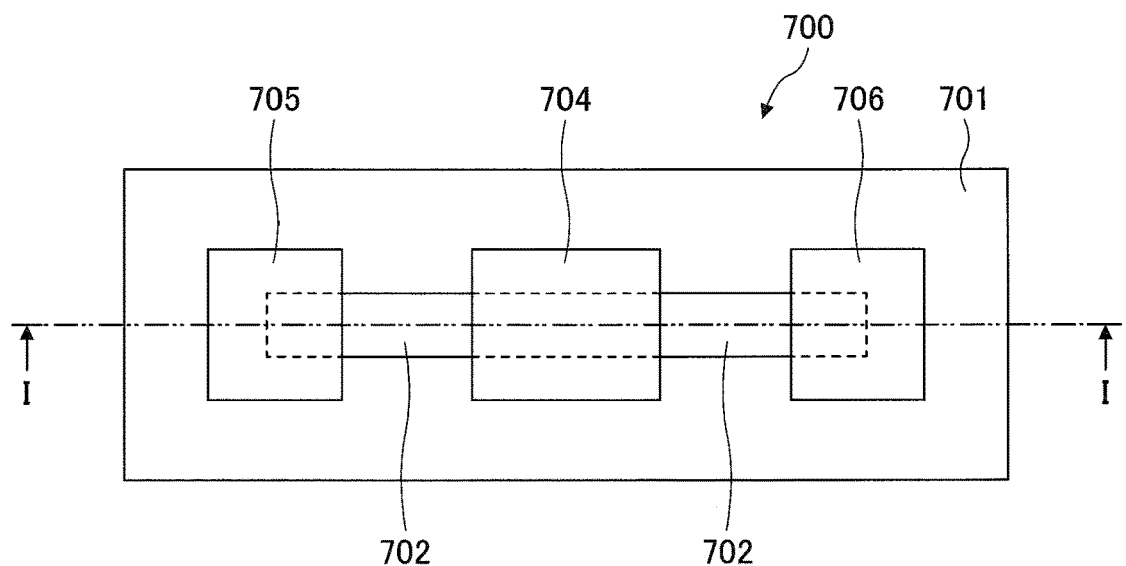
FIG. 18A is a plan view illustrating a semiconductor device according to a seventh embodiment.
Figure 18B:
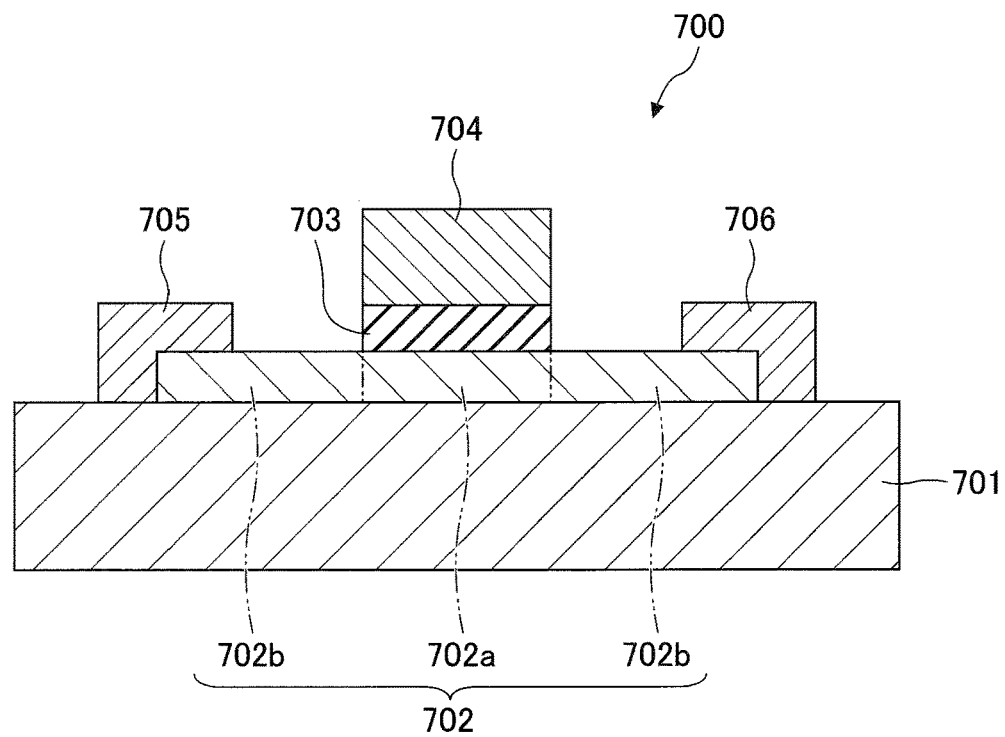
FIG. 18B is a cross sectional view illustrating the semiconductor device according to the seventh embodiment.

Next, a seventh embodiment will be described. The seventh embodiment relates to a semiconductor device including the GNR. FIG. 18A and FIG. 18B respectively are a plan view and a cross sectional view illustrating the semiconductor device according to the seventh embodiment. FIG. 18B corresponds to the cross sectional view along a line I-I in FIG. 18A.

A semiconductor device 700 according to the seventh embodiment includes a silicon substrate 701, a GNR 702, a gate insulating layer 703, a gate electrode 704, a source electrode 705, and a drain electrode 706, as illustrated in FIG. 18A and FIG. 18B. The GNR 702 is provided on the silicon substrate 701. The source electrode 705 contacts one end (first end) of the GNR 702 on the silicon substrate 701, and the drain electrode 706 contacts another end (second end) of the GNR 702 on the silicon substrate 701. The gate insulating layer 703 is provided on the GNR 702 between the source electrode 705 and the drain electrode 706. The gate electrode 704 is provided on the gate insulating layer 703.

The GNR 702 includes a porphyrin GNR part 702a under the gate insulating layer 703, a porphyrin metal complex GNR part 702b arranged closer to the source electrode 705 than the porphyrin GNR part 702a, and a porphyrin metal complex GNR part 702b arranged closer to the drain electrode 706 than the porphyrin GNR part 702a. The porphyrin GNR part 702a and the porphyrin metal complex GNR part 702b are bonded to each other by a carbon-to-carbon bonding at the respective first and second ends of the porphyrin GNR part 702a. The porphyrin metal complex GNR part 702b includes a porphine ring, and a Cu atom is bonded to the N atom of the porphine ring. In other words, the porphyrin GNR part 702a includes the chemical structure of porphyrin, and the porphyrin metal complex GNR part 702b includes the chemical structure of porphyrin metal complex.

Figure 19:
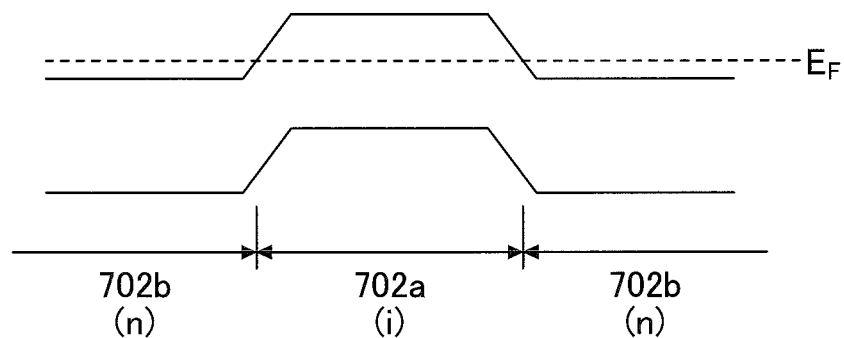
FIG. 19 is a diagram illustrating the band structure of the GNR included in the semiconductor device according to the seventh embodiment.

FIG. 19 is a diagram illustrating a band structure of the GNR 702. As illustrated in FIG. 19, in the porphyrin GNR part 702a, the Fermi level $E_F$ is located between a top of a conduction band and a bottom of a valence band thereof. On the other hand, in the porphyrin metal complex GNR part 702b, the Fermi level $E_F$ is higher than the bottom of the valence band thereof. Accordingly, the porphyrin GNR part 702a exhibits properties of the i-type semiconductor, the porphyrin metal complex GNR part 702b exhibits properties of the n-type semiconductor, and the GNR 702 includes a nin heterojunction.

Hence, the semiconductor device 700 is an example of a top-gate type Field Effect Transistor (FET) having the nin structure and the GNR 702 as a channel layer.

An insulating material, such as silicon oxide ($SiO_2$) or the like, may be used for the gate insulating layer 703. A metal material, such as titanium (Ti), chromium (Cr), cobalt (Co), nickel (Ni), palladium (Pd), aluminum (Al), copper (Cu), silver (Ag), platinum (Pt), gold (Au), or the like, may be used for the gate electrode 704, the source electrode 705, and the drain electrode 706.

According to the seventh embodiment, it is possible to obtain a FET having a simple structure and a small band gap. In addition, by changing the metal atom included in the porphyrin metal complex GNR part 702b to a Ni atom or the like having the Fermi level $E_F$ that is higher than the bottom of the valence band thereof, it becomes possible to adjust the band gap while simultaneously achieving the nin heterojunction.

Next, a method of manufacturing the semiconductor device 700 will be described. FIG. 20A through FIG. 20D are cross sectional views illustrating, in sequence, processes of the method of manufacturing the semiconductor device 700.

Figure 20A:
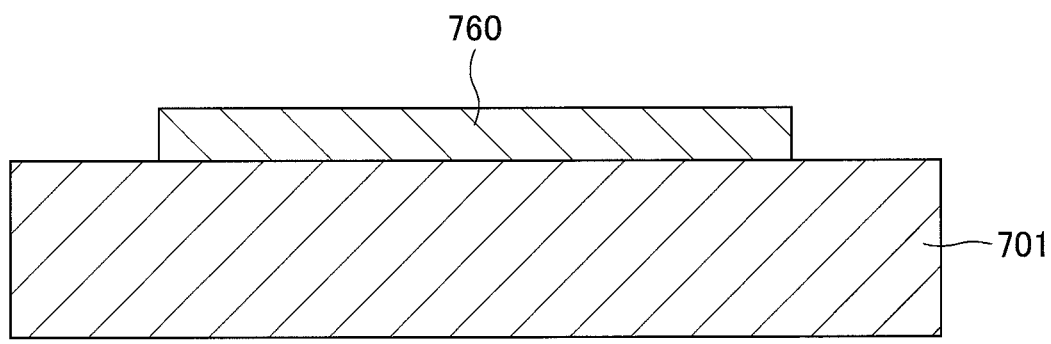
FIG. 20A is a cross sectional view illustrating a method of manufacturing the semiconductor device according to the seventh embodiment.

First, as illustrated in FIG. 20A, the porphyrin GNR 760 is provided on the silicon substrate 701. For example, the porphyrin GNR 760 may be formed on a catalyst metal substrate by bottom-up synthesis, and then transferred onto the silicon substrate 701 using a mending tape or the like.

Figure 20B:
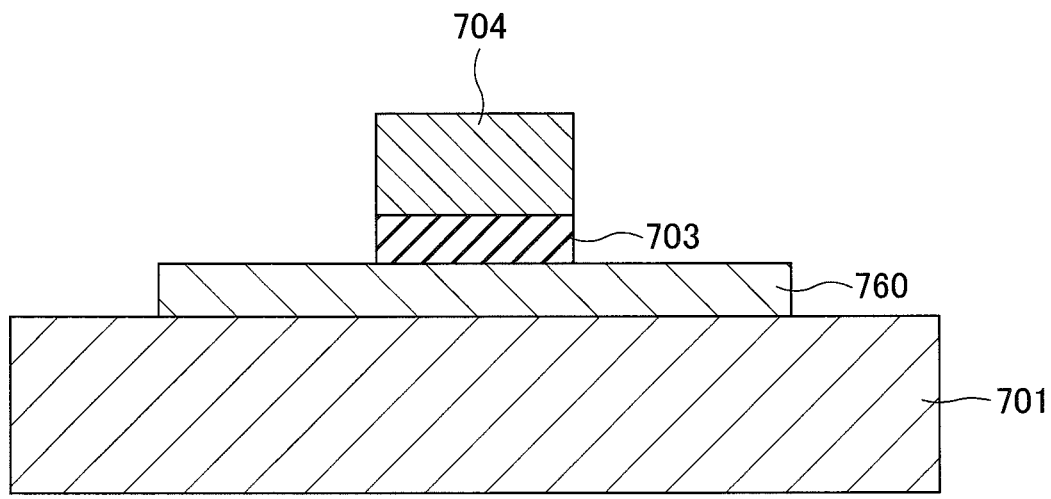
FIG. 20B is a cross sectional view illustrating the method of manufacturing the semiconductor device according to the seventh embodiment.

Next, as illustrated in FIG. 20B, the gate insulating layer 703 and the gate electrode 704 are formed on the silicon substrate 701, so as to cover a region where the porphyrin GNR part 702a of the porphyrin GNR 760 is to be formed. When forming the gate insulating layer 703 and the gate electrode 704, a resist is first patterned using photolithography, to form a resist mask having openings in regions where the gate insulating layer 703 and the gate electrode 704 are to be formed. Then, an Al layer having a thickness of approximate 1 nm, for example, is formed on the resist mask, including the inside of the openings in the resist mask, by a deposition method such as sputtering or the like. This Al layer is used as a seed layer, to deposit an insulating layer of $HfO_2$ or the like, using Atomic Layer Deposition (ALD), to deposit an insulating layer on the Al layer. Thereafter, a metal layer is deposited on the insulating layer using vapor deposition, sputtering, or the like. The metal layer may have a laminated structure including a Ti layer, and a Au layer formed on the Ti layer, for example. Finally, the resist mask, and the insulating layer and the metal layer provided on the resist mask, are removed using lift-off, for example. As a result, it is possible to form the gate insulating layer 703 and the gate electrode 704.

Figure 20C:
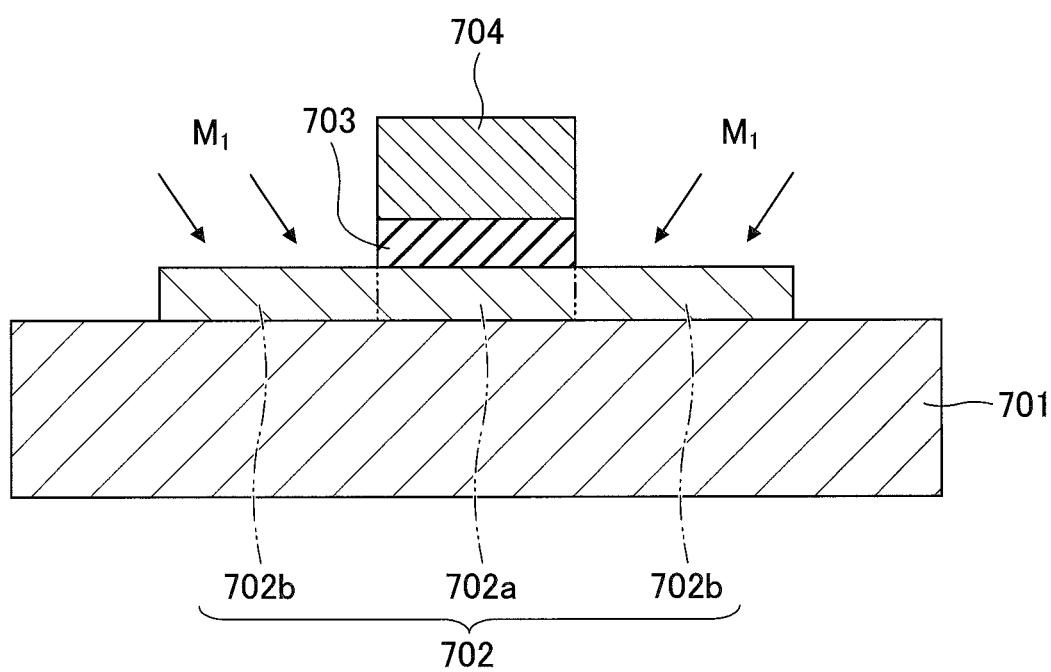
FIG. 20C is a cross sectional view illustrating the method of manufacturing the semiconductor device according to the seventh embodiment.

Thereafter, as illustrated in FIG. 20C, the silicon substrate 701 having the porphyrin GNR 760, the gate insulating layer 703, and the gate electrode 704 formed thereon, is immersed into an organic solvent having dissolved therein the metallic salt of Cu, and the organic solvent is stirred. As a result, the Cu atom bonds to the N atom of the porphine ring, as the metal atom $M_1$, at the regions of the porphyrin GNR 760 where the gate insulating layer 703 and the gate electrode 704 are exposed from the porphyrin GNR 760. Hence, the GNR 702, including the porphyrin GNR part 702a and the porphyrin metal complex GNR part 702b, is formed. The kind of organic solvent used may be an aqueous solution of acetic acid, for example.

Figure 20D:
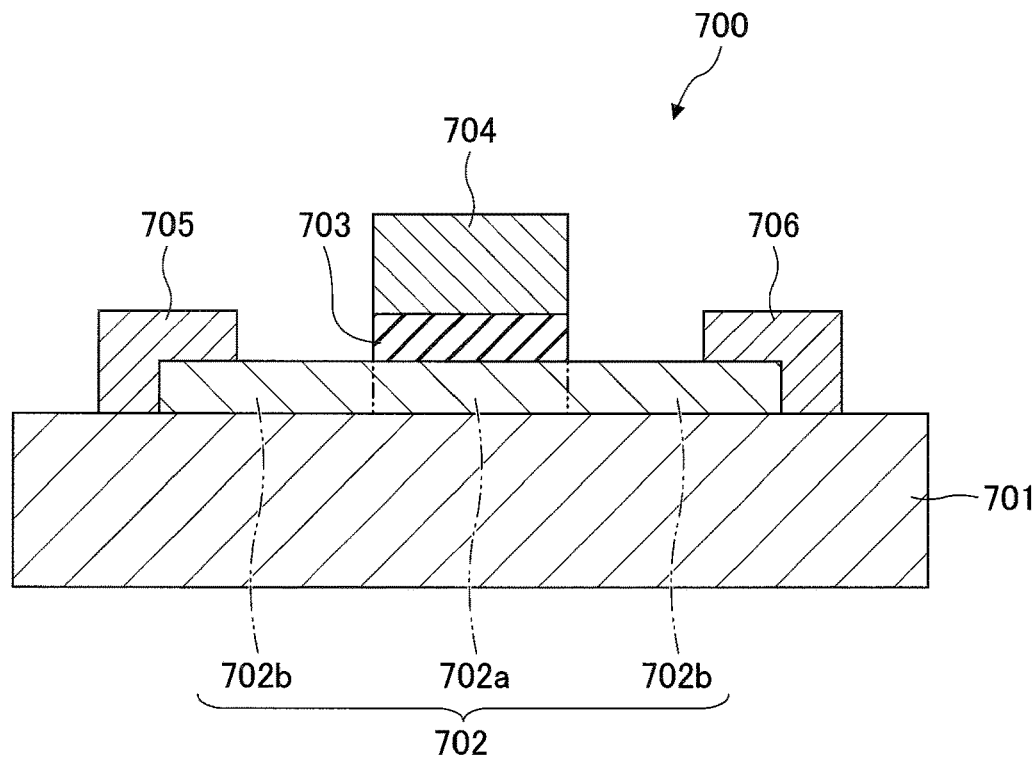
FIG. 20D is a cross sectional view illustrating the method of manufacturing the semiconductor device according to the seventh embodiment.

Next, as illustrated in FIG. 20D, the source electrode 705 that contacts the first end of the GNR 702, and the drain electrode 706 that contacts the second end of the GNR 702, are formed on the silicon substrate 701. When forming the source electrode 705 and the drain electrode 706, a resist is first patterned using photolithography, to form a resist mask having openings in regions where the source electrode 705 and the drain electrode 706 are to be formed. Then, a metal layer is deposited on the resist mask, including the inside of the openings in the resist mask, using vapor deposition, sputtering, or the like. The metal layer may have a laminated structure including a Ti layer, and a Au layer formed on the Ti layer, for example. Finally, the resist mask, and the metal layer provided on the resist mask, are removed using lift-off, for example. As a result, it is possible to form the source electrode 705 and the drain electrode 706.

Hence, the semiconductor device 700 according to the seventh embodiment can be manufactured by the processes described heretofore.

Eighth Embodiment

Figure 21A:
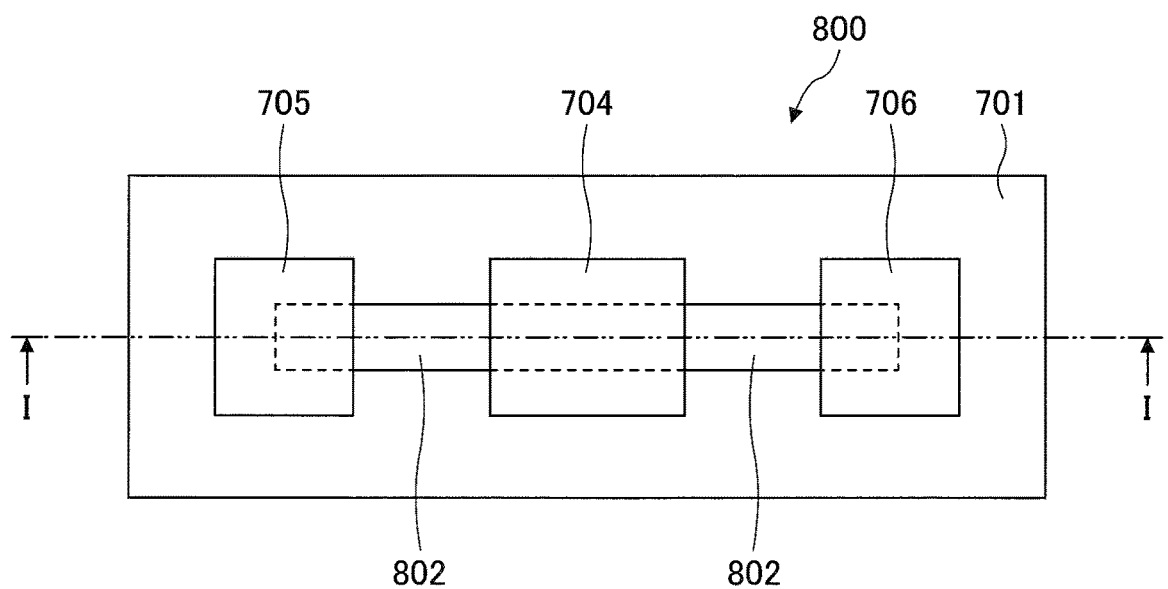
FIG. 21A is a plan view illustrating the semiconductor device according to an eighth embodiment.
Figure 21B:
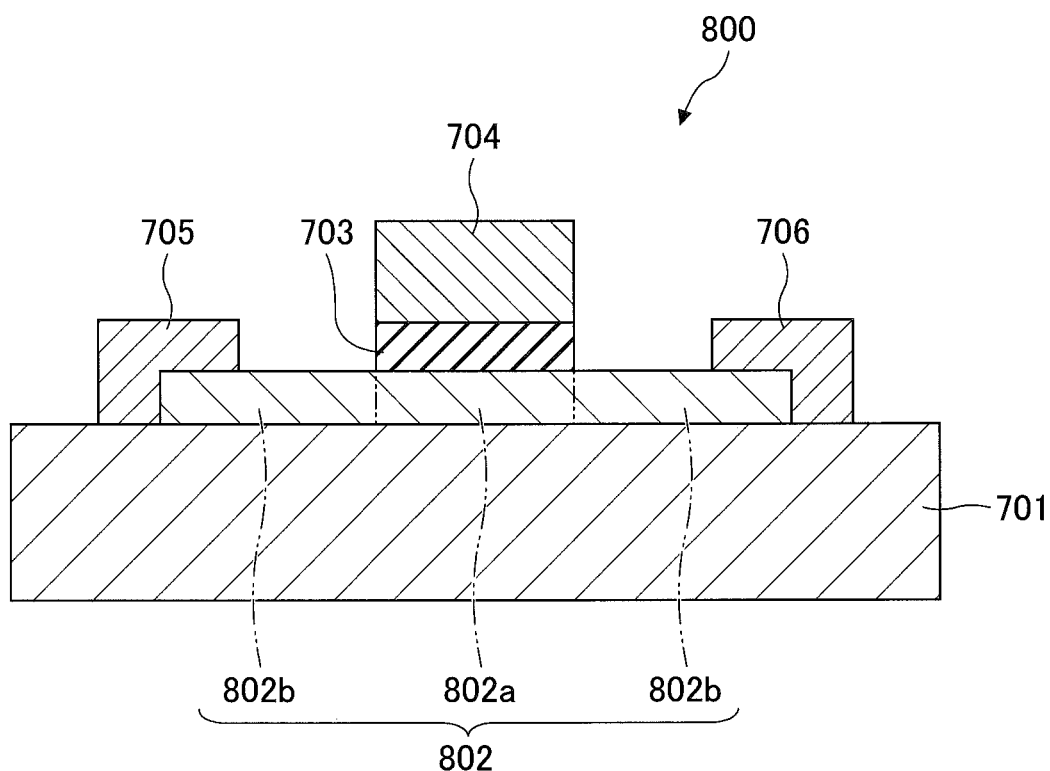
FIG. 21B is a cross sectional view illustrating the semiconductor device according to the eighth embodiment.

Next, an eighth embodiment will be described. The eighth embodiment relates to the semiconductor device including the GNR. FIG. 21A and FIG. 21B respectively are a plan view and a cross sectional view illustrating the semiconductor device according to the eighth embodiment. FIG. 21B corresponds to the cross sectional view along a line I-I in FIG. 21A.

A semiconductor device 800 according to the eighth embodiment includes a GNR 802 in place of the GNR 702, as illustrated in FIG. 21A and FIG. 21B. Otherwise, the structure of the eight embodiment is the same as the structure of the seventh embodiment. The GNR 802 includes a porphyrin metal complex GNR part 802a under the gate insulating layer 703, a porphyrin metal complex GNR part 802b arranged closer to the source electrode 705 than the porphyrin metal complex GNR part 802a, and a porphyrin metal complex GNR part 802b arranged closer to the drain electrode 706 than the porphyrin metal complex GNR part 802a. The porphyrin metal complex GNR part 802a and the porphyrin metal complex GNR part 802b are bonded to each other by a carbon-to-carbon bonding at the respective first and second ends of the porphyrin metal complex GNR part 802a. The porphyrin metal complex GNR part 802a includes a porphine ring, and a Zn atom is bonded to the N atom of the porphine ring. The porphyrin metal complex GNR parts 802b include a porphine ring, and a Cu atom is bonded to the N atom of the porphine ring.

Figure 22:
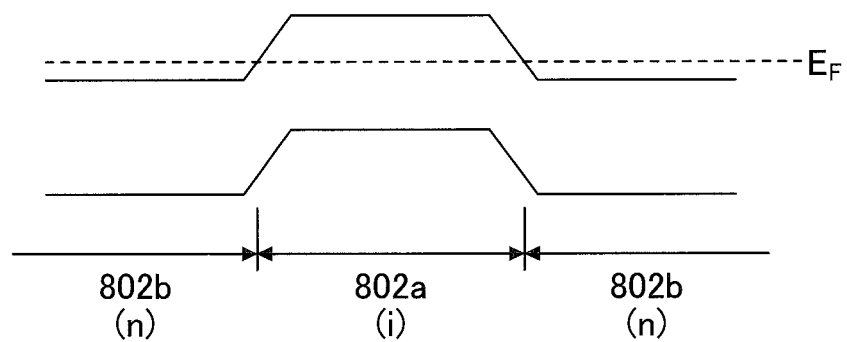
FIG. 22 is a diagram illustrating the band structure of the GNR included in the semiconductor device according to the eighth embodiment.

FIG. 22 is a diagram illustrating a band structure of the GNR 802. As illustrated in FIG. 22, in the porphyrin metal complex GNR part 802a, the Fermi level $E_F$ is located between a top of a conduction band and a bottom of a valence band thereof. On the other hand, in the porphyrin metal complex GNR part 802b, the Fermi level $E_F$ is higher than the bottom of the valence band thereof. Accordingly, the porphyrin metal complex GNR part 802a exhibits properties of the i-type semiconductor, the porphyrin metal complex GNR part 802b exhibits properties of the n-type semiconductor, and the GNR 802 includes a nin heterojunction.

Hence, the semiconductor device 800 is an example of a top-gate type FET having the nin structure and the GNR 802 as the channel layer.

According to the eighth embodiment, it is possible to obtain a FET having a simple structure and a small band gap. In addition, by changing the metal atom included in the porphyrin metal complex GNR part 802b to a Ni atom or the like having the Fermi level $E_F$ that is higher than the bottom of the valence band thereof, it becomes possible to adjust the band gap while simultaneously achieving the nin heterojunction. Further, by changing the metal atom included in the porphyrin metal complex GNR part 802a to another atom having the Fermi level $E_F$ that is located between the top of the conduction band and the bottom of the valence band thereof, it becomes possible to adjust the band gap while simultaneously achieving the nin heterojunction.

Next, a method of manufacturing the semiconductor device 800 will be described. FIG. 23A through FIG. 23D are cross sectional views illustrating, in sequence, processes of the method of manufacturing the semiconductor device 800.

Figure 23A:
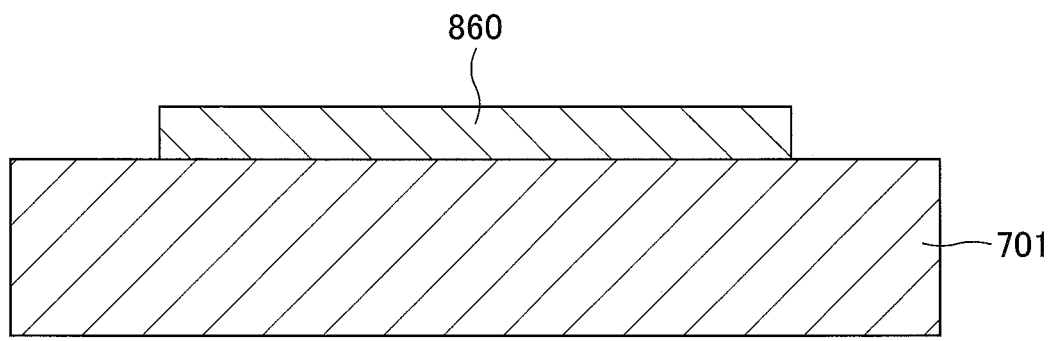
FIG. 23A is a cross sectional view illustrating a method of manufacturing the semiconductor device according to the eighth embodiment.

First, as illustrated in FIG. 23A, the porphyrin metal complex GNR 860 in which the Zn atom is bonded to the N atom of the porphine ring, is provided on the silicon substrate 701. For example, the porphyrin metal complex GNR 860 may be formed on a catalyst metal substrate by bottom-up synthesis, and then transferred onto the silicon substrate 701 using a mending tape or the like.

Figure 23B:
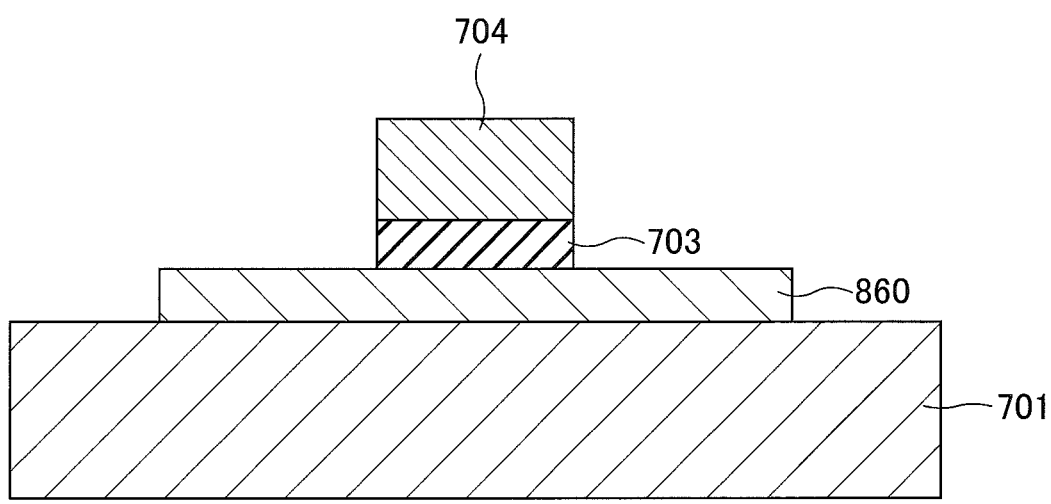
FIG. 23B is a cross sectional view illustrating the method of manufacturing the semiconductor device according to the eighth embodiment.

Next, as illustrated in FIG. 23B, the gate insulating layer 703 and the gate electrode 704 are formed on the silicon substrate 701, so as to cover a region where the porphyrin metal complex GNR part 802a of the porphyrin GNR 860 is to be formed.

Figure 23C:
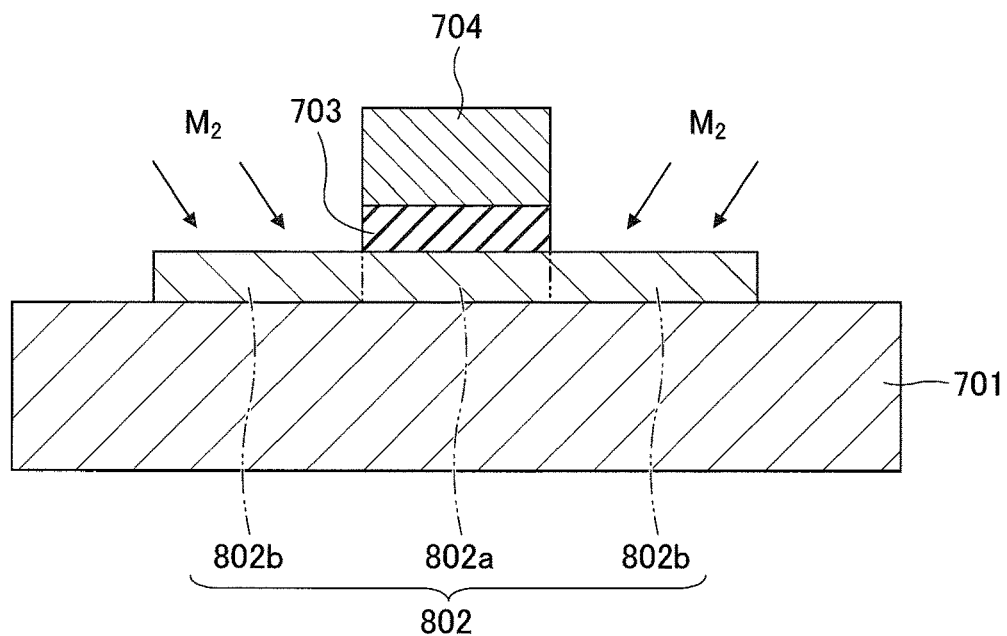
FIG. 23C is a cross sectional view illustrating the method of manufacturing the semiconductor device according to the eighth embodiment.

Thereafter, as illustrated in FIG. 23C, the silicon substrate 701 having the porphyrin metal complex GNR 860, the gate insulating layer 703, and the gate electrode 704 formed thereon, is immersed into an organic solvent having dissolved therein the metallic salt of Cu, and the organic solvent is stirred. As a result, the Cu atom bonds to the N atom of the porphine ring, as the metal atom $M_2$ in place of the Zn atom, at the regions of the porphyrin metal complex GNR 860 where the gate insulating layer 703 and the gate electrode 704 are exposed from the porphyrin metal complex GNR 860. Hence, the GNR 802, including the porphyrin metal complex GNR part 802a and the porphyrin metal complex GNR part 802b, is formed. The kind of organic solvent used may be an aqueous solution of acetic acid, for example.

Figure 23D:
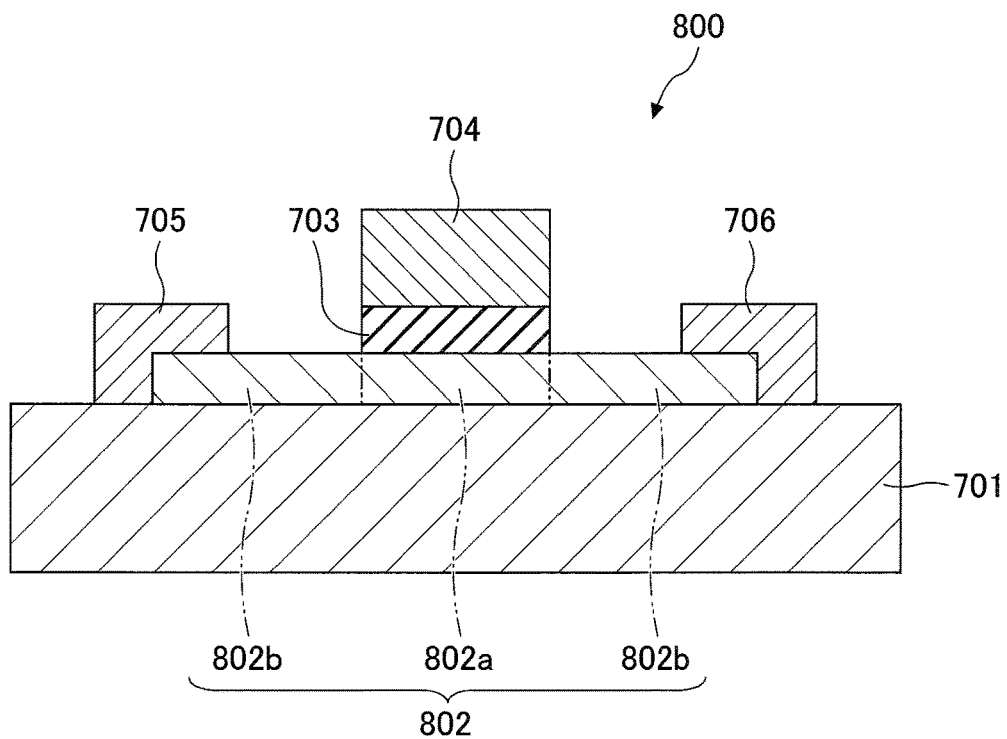
FIG. 23D is a cross sectional view illustrating the method of manufacturing the semiconductor device according to the eighth embodiment.

Next, as illustrated in FIG. 23D, the source electrode 705 that contacts the first end of the GNR 802, and the drain electrode 706 that contacts the second end of the GNR 802, are formed on the silicon substrate 701.

Hence, the semiconductor device 800 according to the eighth embodiment can be manufactured by the processes described heretofore.

In each of the embodiments described above, acene included in the units is not limited to anthracene, and the acene may be naphthalene, tetracene, or the like. In addition, in each of the nanoribbons according to the embodiments, the terminal group is not particularly limited. For example, the terminal group of the nanoribbon synthesized from the precursor molecule illustrated in FIG. 4A, may include a hydrogen or halogen atom bonded with respect to the plurality of carbon atoms located at the end of the nanoribbon, similar to the precursor molecule of FIG. 4A, or alternatively, the hydrogen atom may be bonded to all of plurality of carbon atoms located at the end of the nanoribbon. In the seventh and eighth embodiments, a porphyrin nanoribbon may be used in place of the GNR.

The usage of the semiconductor devices described heretofore is not particularly limited. For example, the semiconductor devices may be used for high-power amplifiers for wireless base stations, high-power amplifiers for mobile phone base stations, semiconductor elements for servers, semiconductor elements for personal computers, on-board Integrated Circuits (ICs) for vehicles, motor driving transistors for electric vehicles, or the like.

According to each of the embodiments described above, it is possible to obtain various electron states.

Although the embodiments are numbered with, for example, "first," "second," "third," "fourth," "fifth," "sixth," "seventh," or "eighth," the ordinal numbers do not imply priorities of the embodiments. Many other variations and modifications will be apparent to those skilled in the art.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A nanoribbon comprising:

a structure represented by a structural formula (8), where $M_1$ is a metal atom, g, p, q, r, s, t, and u are mutually independent and are integers greater than or equal to 1, $R^1$, $R^2$, $R^3$, $R^4$, $R^5$, $R^6$, $R^7$, and $R^8$ are mutually independent and are one of a hydrogen atom, a substituent, an alkyl moiety, a phenyl moiety, and a halogen atom, the substituent is selected from a group consisting of a hydroxyl group, a nitro group, an amino group, a formyl group, a carboxyl group, and a sulfonyl group, and A is a hydrogen atom or an aryl group

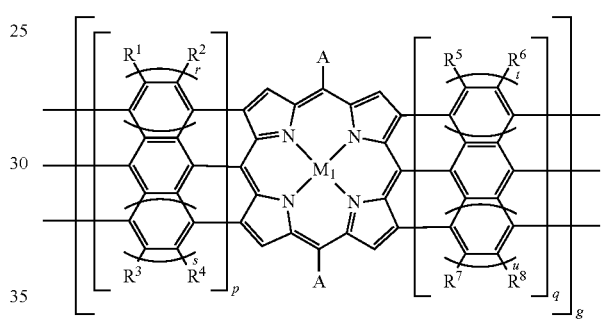

(8)

2. A nanoribbon comprising:

a first unit having a structure including an arrangement of a plurality of first sub-units respectively including a structure represented by a structural formula (10); and a second unit having a structure including an arrangement of a plurality of second sub-units respectively including a structure represented by a structural formula (11), wherein the first unit and the second unit are mutually bonded by a carbon-to-carbon bonding between an end of the first unit and an end of the second unit, wherein $M_1$ is a metal atom, and A is a hydrogen atom or an aryl group,

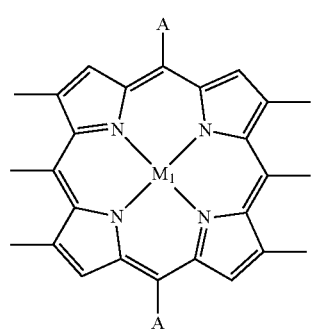

(10)

-continued (11)

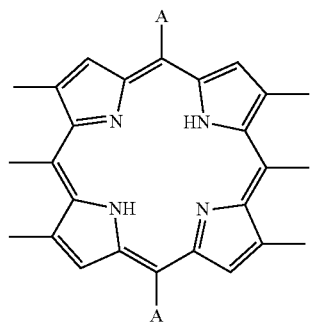

wherein the first unit has the structure represented by a structural formula (13) in which g, p, q, r, s, t, and u are mutually independent and are integers greater than or equal to 1, $R^1$, $R^2$, $R^3$, $R^4$, $R^5$, $R^6$, $R^7$, and $R^8$ are mutually independent and are one of a hydrogen atom, a substituent, an alkyl moiety, a phenyl moiety, and a halogen atom, the substituent is selected from a group consisting of a hydroxyl group, a nitro group, an amino group, a formyl group, a carboxyl group, and a sulfonyl group, and A is a hydrogen atom or an aryl group, and (13)

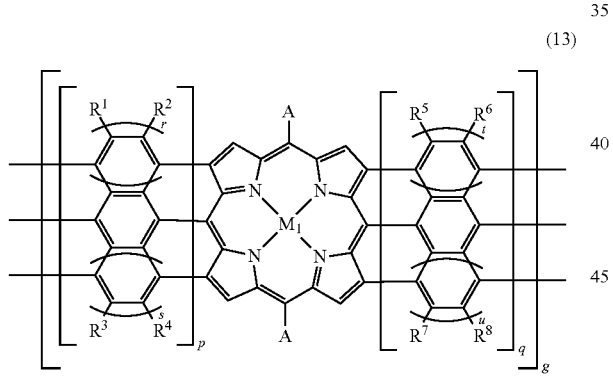

wherein the second unit has the structure represented by a structural formula (14) in which h, p, q, r, s, t, and u are mutually independent and are integers greater than or equal to 1, $R^1$, $R^2$, $R^3$, $R^4$, $R^5$, $R^6$, $R^7$, and $R^8$ are mutually independent and are one of a hydrogen atom, a substituent, an alkyl moiety, a phenyl moiety, and a halogen atom, the substituent is selected from a group consisting of a hydroxyl group, a nitro group, an amino group, a formyl group, a carboxyl group, and a sulfonyl group, and A is a hydrogen atom or an aryl group (14)

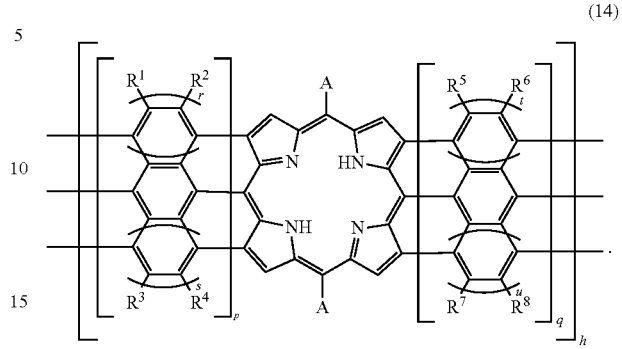

3. The nanoribbon as claimed in claim 2, wherein at least the plurality of first sub-units or the plurality of second sub-units further include at least one structure represented by a structural formula (16), p, r, and s are mutually independent and are integers greater than or equal to 1, $R^1$, $R^2$, $R^3$, and $R^4$ are mutually independent and are one of a hydrogen atom, a substituent, an alkyl moiety, a phenyl moiety, and a halogen atom, and the substituent is selected from a group consisting of a hydroxyl group, a nitro group, an amino group, a formyl group, a carboxyl group, and a sulfonyl group (16)

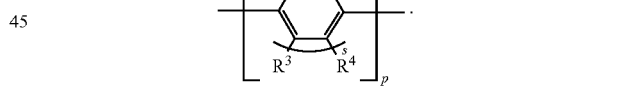

4. The nanoribbon as claimed in claim 2, wherein the first unit and the second unit are periodically arranged.

5. A nanoribbon comprising:

a first unit having a structure including an arrangement of a plurality of first sub-units respectively including a structure represented by a structural formula (10); and a second unit having a structure including an arrangement of a plurality of second sub-units respectively including a structure represented by a structural formula (12), wherein the first unit and the second unit are mutually bonded by a carbon-to-carbon bonding between an end of the first unit and an end of the second unit, wherein $M_1$ and $M_2$ are mutually different metal atoms, and A is a hydrogen atom or an aryl group, (10)

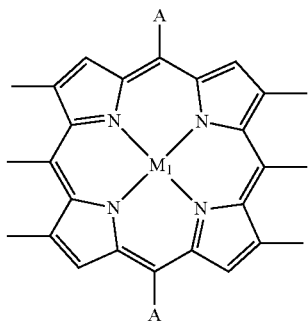

(12)

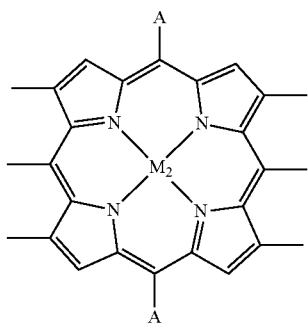

wherein the first unit has the structure represented by a structural formula (13) in which
  g, p, q, r, s, t, and u are mutually independent and are integers greater than or equal to 1,
  $R^1$, $R^2$, $R^3$, $R^4$, $R^5$, $R^6$, $R^7$, and $R^8$ are mutually independent and are one of a hydrogen atom, a substituent, an alkyl moiety, a phenyl moiety, and a halogen atom,
  the substituent is selected from a group consisting of a hydroxyl group, a nitro group, an amino group, a formyl group, a carboxyl group, and a sulfonyl group, and
  A is a hydrogen atom or an aryl group, and (13)

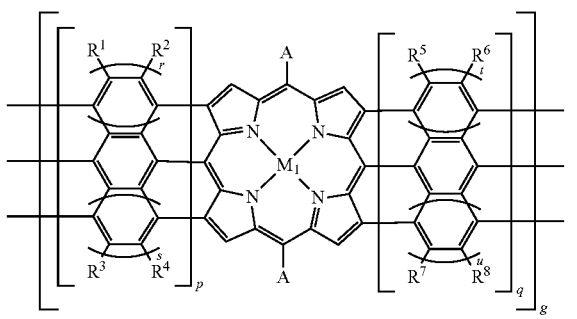

wherein the second unit has the structure represented by a structural formula (15) in which
  h, p, q, r, s, t, and u are mutually independent and are integers greater than or equal to 1,
  $R^1$, $R^2$, $R^3$, $R^4$, $R^5$, $R^6$, $R^7$, and $R^8$ are mutually independent and are one of a hydrogen atom, a substituent, an alkyl moiety, a phenyl moiety, and a halogen atom,
  the substituent is selected from a group consisting of a hydroxyl group, a nitro group, an amino group, a formyl group, a carboxyl group, and a sulfonyl group, and
  A is a hydrogen atom or an aryl group (15)

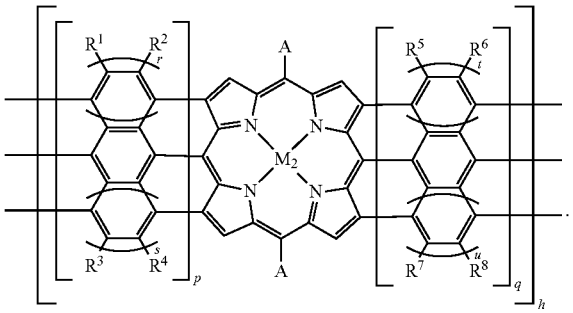

6. The nanoribbon as claimed in claim 5, wherein
  at least the plurality of first sub-units or the plurality of second sub-units further include at least one structure represented by a structural formula (16),
  p, r, and s are mutually independent and are integers greater than or equal to 1,
  $R^1$, $R^2$, $R^3$, and $R^4$ are mutually independent and are one of a hydrogen atom, a substituent, an alkyl moiety, a phenyl moiety, and a halogen atom, and
  the substituent is selected from a group consisting of a hydroxyl group, a nitro group, an amino group, a formyl group, a carboxyl group, and a sulfonyl group (16)

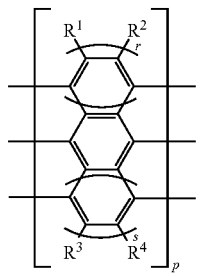

7. The nanoribbon as claimed in claim 5, wherein the first unit and the second unit are periodically arranged.

* * * * *